(12) United States Patent
Mansmann

(10) Patent No.: US 8,652,173 B2
(45) Date of Patent: Feb. 18, 2014

(54) ADJUSTABLE RACHETING SUTURE ANCHORS

(75) Inventor: Kevin A. Mansmann, Paoli, PA (US)

(73) Assignee: Formae, Inc., Paoli, PA (US)

(*) Notice: Subject to any disclaimer, the term of this patent is extended or adjusted under 35 U.S.C. 154(b) by 119 days.

(21) Appl. No.: 13/355,276

(22) Filed: Jan. 20, 2012

(65) Prior Publication Data
US 2013/0190815 A1 Jul. 25, 2013

Related U.S. Application Data

(60) Provisional application No. 61/434,145, filed on Jan. 19, 2011.

(51) Int. Cl.
*A61B 17/04* (2006.01)
*A61B 17/06* (2006.01)

(52) U.S. Cl.
USPC ............ 606/232; 606/224; 606/225; 606/226

(58) Field of Classification Search
CPC ............... A61B 2017/0446; A61B 2017/0448; A61B 2017/0451; A61B 2017/0454; A61B 2017/0456
USPC .................................. 606/232, 224, 225, 226
See application file for complete search history.

(56) References Cited

U.S. PATENT DOCUMENTS

| | | | |
|---|---|---|---|
| 6,328,758 B1 | 12/2001 | Tornier | |
| 6,520,980 B1 | 2/2003 | Foerster | |
| 6,540,770 B1 | 4/2003 | Tornier | |
| 6,585,730 B1 | 7/2003 | Foerster | |
| 7,144,415 B2 | 12/2006 | Del Rio | |
| 7,390,329 B2 * | 6/2008 | Westra et al. | ................. 606/151 |
| 7,556,640 B2 | 7/2009 | Foerster | |
| 7,572,283 B1 | 8/2009 | Meridew | |
| 7,637,926 B2 | 12/2009 | Foerster | |
| 7,682,374 B2 | 3/2010 | Foerster | |
| 7,695,494 B2 | 4/2010 | Foerster | |

(Continued)

FOREIGN PATENT DOCUMENTS

WO 0074554 A2 12/2000

OTHER PUBLICATIONS

European Search Report, EP 2617391A3, Jul. 31, 2013.

*Primary Examiner* — Katherine Dowe
*Assistant Examiner* — Michael Mendoza
(74) *Attorney, Agent, or Firm* — Duane Morris LLP

(57) ABSTRACT

Knotless suture anchors are disclosed for surgical use, which contain one or more types of ratcheting mechanisms that will allow a surgeon to pull a suture strand through an anchor device in one direction, without allowing the suture strand to travel or creep backward, in the other direction. This will allow a surgeon to emplace a number of such anchors in hard bone(s) or soft tissue(s), during installation of an implant device, while the various suture strands remain loose and do not interfere with proper positioning of the implant. When the implant device is roughly in position, the surgeon can gently "snug" all of the suture strands (which preferably should be braided, to provide a non-smooth surface that will enable a stronger and more secure grip by the ratcheting mechanism), so that they will all reach a moderate plateau of gentle yet firm tension. After the surgeon has ensured that the implant is in proper position, with all of the anchoring sutures in a "snug" status, a series of final tightening and tensioning steps can be carried out on all of the suture strands.

6 Claims, 9 Drawing Sheets

(56) References Cited

U.S. PATENT DOCUMENTS

| | | |
|---|---|---|
| 2002/0173855 A1 | 11/2002 | Mansmann |
| 2003/0130695 A1 | 7/2003 | McDevitt |
| 2005/0090827 A1* | 4/2005 | Gedebou .................. 606/72 |
| 2006/0106423 A1* | 5/2006 | Weisel et al. ............. 606/232 |
| 2007/0224238 A1 | 9/2007 | Mansmann |
| 2009/0132047 A1 | 5/2009 | Mansmann |
| 2010/0063542 A1 | 3/2010 | van der Burg |
| 2010/0121348 A1 | 5/2010 | van der Burg |
| 2011/0224801 A1 | 9/2011 | Mansmann |

* cited by examiner

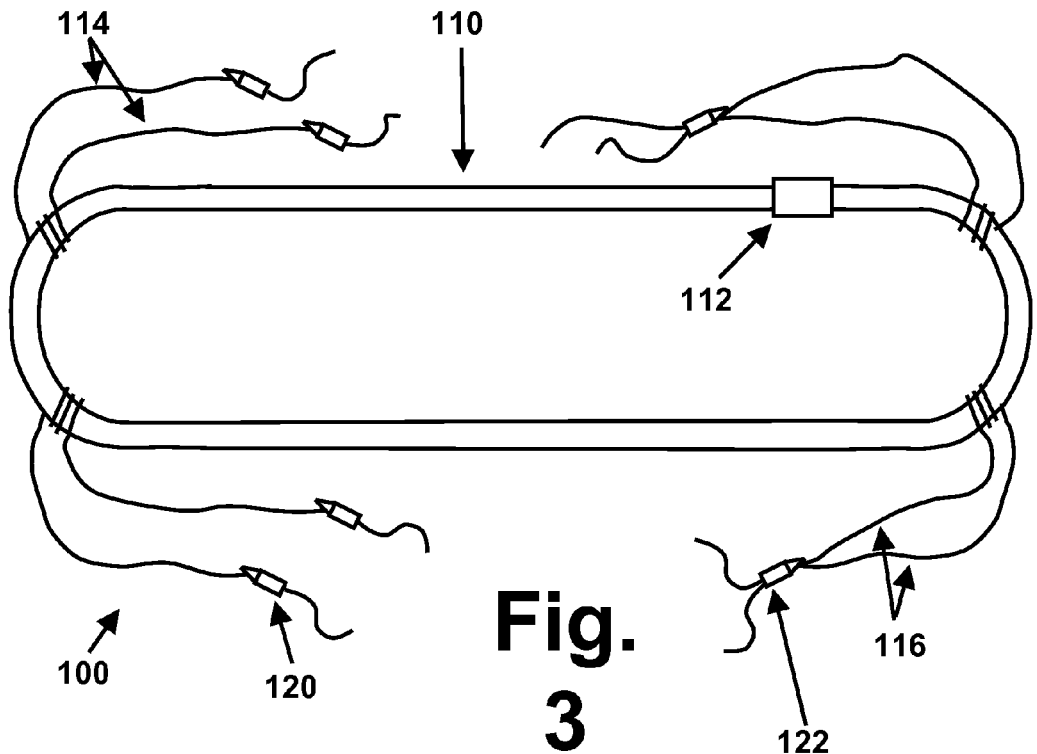
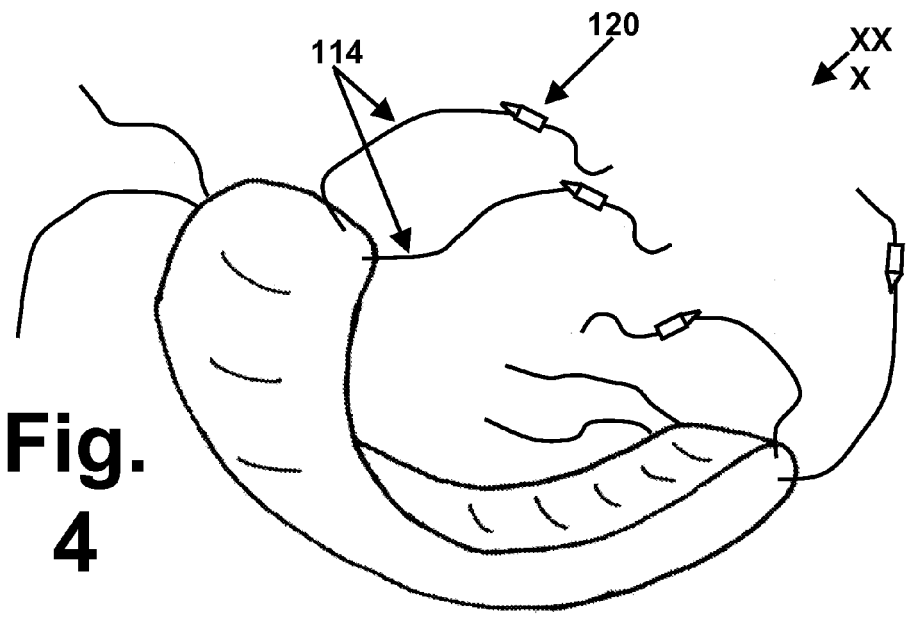

ADJUSTABLE RACHETING SUTURE ANCHORS

RELATED APPLICATION

This application claims priority under 35 USC 119 based on provisional application No. 61/434,145, filed on Jan. 19, 2011.

BACKGROUND

This invention is in the field of surgical devices that will be implanted into human or animal bodies, for uses such as repairing or replacing cartilage in joints such as knees or hips, or for repairing injuries to tendons, ligaments, or other connective tissues.

Efforts have been made to design and create various types of surgical devices called "knotless suture anchors". A subgroup of such devices which are of interest herein are designed to attach soft tissues (such as ligaments or tendons) to hard bones. These are used mainly by orthopedic surgeons, and by other physicians who specialize in "sports medicine". These practitioners make every effort to minimize any cutting of (and any damage to) the tendons, ligaments, muscles, blood vessels, and other soft tissues that surround injured, diseased, or otherwise damaged or defective tissue, especially in and around articulating joints. Therefore, any steps that can be taken to minimize the number and the lengths (or sizes) of any incisions and cuts that must be made, during arthroscopic or other surgical repair of joints and other structures, are regarded as useful and helpful.

In addition, orthopedic surgeons are under pressure to work as quickly and efficiently as possible, starting when a patient's skin has been cut or punctured by the first instrument, and lasting until the patient's joint, limb, or body has been closed up and covered with bandages. As a general principle, the longer a patient's body or limb stays open, the greater will be the risk, threat, and likelihood of infection.

Accordingly, the requirement of having to tie knots in suture strands, when the only instruments that can be used are long arthroscopic instruments that are narrow enough to pass through a small arthroscopic incision, can pose difficult challenges. These challenges become especially complex, when one realizes that typical arthroscopic surgery requires, in addition to the actual surgical instruments, a number of supporting devices, which in most cases will include: (i) a light source; (ii) a camera with a live video feed, which normally will use fiber-optic cables; (iii) a tube which will continuously pump clear saline liquid into the joint or other operating area, to carry blood and debris out of area so that the surgeon can see the structures and tissues that are being manipulated; and, (iv) a drainage catheter or cannula, to suction the saline liquid and its contents out of the joint or body cavity.

Under those conditions, the challenge of tying a knot in a suture strand, especially in a location that may be on the far (distal) side of a bone or other anatomic structure, using only a single elongated instrument tip, can become be extremely difficult, and can be compared to trying to tie a set of shoelaces into a tight and secure knot, using a set of needle-nosed pliers that can be touched by only one hand.

Surgical staples can be well-suited for securing soft tissues to other soft tissues, but they are not suited for securing soft tissues (or suture strands which have been attached to soft tissues) to hard bone surfaces. When attachments to hard bone are required, more secure devices, usually called anchors, are used instead of staples. Some are designed to be screwed or tapped into a "pilot hole" that has been drilled into a bone; others are driven directly into a bone surface, in a manner comparable to driving a nail into a board with no pilot hole.

Accordingly, surgeons and orthopedic supply companies have developed various types of "knotless suture anchors", which enable surgeons to attach suture strands (which, in most cases, will be attached to soft tissues, and which can thereby provide convenient "handles" that can be used to pull, stretch, pin down, or otherwise manipulate the soft tissues) to hard bone surfaces. These types of knotless suture anchors are described and illustrated in a number of issued patents and published patent applications, which can be divided into several categories, for purposes of analyzing and understanding them.

A first category involves anchors that will undergo some type of shape alteration, after they have been inserted into a drilled hole, in a manner which will cause a set of projections to extend outwardly from the main body of the anchor. The projections will press against or dig into the walls of the pilot hole in the bone, thereby firmly securing the anchor to the bone and preventing it from being pulled out by any tensile forces which are likely to be imposed on the suture strand. On some of these types of anchors, the projections have spring-type or angled structures that are similar to the "barbs" on a harpoon or fishing hook; on other anchors in this category, the projections are more closely comparable to the types of "expander bolts" that are used to mount large paintings and other heavy wall-hangings to drywall in homes and other buildings. Issued patents which describe these types of suture anchors include, for example, U.S. Pat. No. 6,328,758 (Tornier et al 2001), U.S. Pat. No. 7,144,415 (Del Rio et al 2006), and U.S. Pat. Nos. 7,556,640 and 7,695,494 (both by Foerster et al, 2009 and 2010).

A second category of knotless suture anchors include two components which are separate from each other before installation. Because of how they interact and function, the two components can be regarded as a receptacle, and an insert. In this type of design, the receptacle component is implanted into a bone, normally into a pilot hole. After the receptacle component has been fully inserted into the bone, the insert component is inserted into the receptacle, typically using tapping, screwing, or similar efforts to drive the insert far enough into the receptacle to lock them together. In some of these anchors, the receptacle component will be fully anchored to the bone, before the insert component is emplaced in the receptacle; in other designs, the act of forcing the insert into the receptacle will cause a shape change which completes the anchoring of the receptacle to the bone.

In these types of knotless suture anchors, a suture strand typically is looped around, passed through, or otherwise coupled or affixed to the insert component, before the insert component is inserted into the receptacle. In some designs, the act of driving the insert into the receptacle will squeeze, crimp, or otherwise secure the suture strand to the anchor, in a manner which cannot be altered later without difficulty; an example of this type of design is provided by U.S. Pat. No. 7,572,283 (Meridew 2009). In other designs, a yielding elastomeric fit between the insert and the receptacle will allow subsequent adjustments to the suture strand, if a tensile force is exerted on the strand which exceeds some type of "threshold" force level; this design is illustrated in several published applications by McDevitt et al, such as US 2003/0130695. Still other designs enable the insert component to be manipulated in a way that will allow the receptacle component to be removed from the bone, if needed, in case the tension on the suture strand which is held by that anchor needs to be adjusted after an initial fixation; this type of design is illustrated by U.S. Pat. No. 6,540,770 (Tornier et al 2003).

Other designs for knotless suture anchors with various other traits are provided by a number of other issued patents and published applications, which include, for example, U.S. Pat. Nos. 6,520,980; 6,585,730; 7,682,374; and 7,637,926, all issued to Foerster et al and assigned to either Opus Medical Inc. or ArthroCare Corporation.

A different type of design, which involves a ratcheting suture anchor, is described and illustrated in two published patent applications, US 2010/0063542 and 2010/0121348, both by Van Der Burg et al. In this design, a suture strand is wrapped around an internal component which can rotate, in a ratcheting manner, within an outer sleeve component. The ratcheting mechanism is provided by a pin, affixed to the top of the rotating internal component, which travels along a sawtooth surface provided by the outer sleeve. The pin can "ride up" each sloped incline on the sawtooth surface. Each time it reaches the top of an incline, it will drop down a steep edge, into a settling location. This effectively prevents the ratchet mechanism from traveling in the non-allowed direction, unless the surgeon takes special steps to disengage the pin from the sawtooth surface so that the tension on the suture strand can be adjusted.

Since this current invention involves different designs for ratcheting suture anchors, the two published Van der Burg applications establish the closest and most directly relevant prior art which is known to the applicant herein.

The types of ratcheting suture anchors disclosed herein were initially conceived and developed, as part of an effort to develop a complete system for a very different type of surgical operation, which involves replacing cartilage segments in joints such as knees, rather than reattaching tendons to bones for purposes such as rotator cuff repair. Because of certain operating requirements and constraints that arise in the types of cartilage repair operations being developed by the Applicant herein, he began with a completely different design, compared to the approach disclosed by Van der Burg et al. Subsequently, after locating and reviewing the Van der Burg applications, the Applicant herein realized that there are major differences in the two approaches to creating ratcheting suture anchors, and that the designs disclosed herein can offer a number of advantages, compared to Van der Burg's approach.

To adequately explain how and why the Applicant's designs took a different approach and arrived at a different set of solutions to a set of challenges and obstacles, some additional background information is required, on how injured or diseased cartilage segments are repaired, in load-bearing joints such as knees and hips.

Hyaline, Meniscal, and Labral Cartilage Segments in Joints

Two different classes of cartilage are essential for the proper functioning of articulating joints. The type of cartilage known as hyaline cartilage forms a relatively thin coating layer of soft and lubricated tissue that covers a "condylar" surface of a bone, in a joint. Two or more segments of hyaline cartilage, on the surfaces of different bones in a joint, will press, rub, and slide against each other, during motion of the joint. Any segment of hyaline cartilage will necessarily have: (i) an "articulating" surface, which is smooth and slippery, and which is kept wet and lubricated by synovial fluid; and, (ii) at least one "anchoring" surface, which create a strong and stabilized interface (reinforced by numerous fibrous proteins and similar components) between the supporting hard bone structure, and the softer layer of cartilage.

Meniscal cartilage is more complicated. Each knee joint contains two meniscal segments, which are generally wedge-shaped arcs that are positioned on the inner (medial) and outer (lateral) sides of the uppermost "plateau" of a tibial bone (i.e., the shinbone). These two wedge-shaped arcs help constrain the femoral bone (i.e., the thighbone), and they help prevent unwanted lateral movement of the femur, across the tibial plateau. Accordingly, the two meniscal segments are not thin layers of cartilage which coat a bone surface; instead, they are fibro-cartilage segments with substantial thickness, and they are kept in position in a "floating but tied down" manner which presses against and stabilizes the medial and lateral sides of the femoral bone. This anchoring attachment is created by a combination of: (i) tendon-like fibrous strands which emerge from both tips of each meniscal arc, and which are attached to bony protrusions located in the middle of the tibial plateau; and, (ii) additional fibers which attach the rounded outer surfaces of the meniscal segments to the soft membranous tissue which forms a watertight capsule that encloses the knee joint. In addition, the geometric structures of the bones also help stabilize the knee joint. Those bone structures include: (i) a "double-roller with center groove" shape, at the bottom condylar end of a femur bone; (ii) an elevated "spine" component in the center of the tibial plateau, which interacts with the center groove on the femoral condyle; and, (iii) a "scalloped" shape on the posterior side of the kneecap (patella), which presses and slides against the double-roller surface on the femur bone.

In addition to meniscal cartilage in knee joints, hip and shoulder joints contains similar relatively thick fibrocartilage segments which are anchored to bones, mainly by indirect means involving tendon-like fibrous supports. Those types of cartilage segments in hip and shoulder joints are called labrum segments, or labral cartilage. For various reasons, they do not require repair or replacement as often as meniscal cartilage segments in knee joints; nevertheless, they do sometimes become injured or degraded, usually in connection with other problems that arise in hip or shoulder joints, and they sometimes need to be surgically repaired or replaced. Because of the structural similarities between meniscal cartilage segments and labral cartilage segments, labral cartilage is regarded and referred to herein as a subtype or subclass of meniscal cartilage, and any references herein to methods or devices for repairing or replacing meniscal cartilage are intended to also cover and include methods and devices for repairing or replacing labral cartilage segments, in hips or shoulders.

It also should be understood that "articulating" joints require two or more bone surfaces to be able to press, move, and slide relative to each other, in a lubricated and frictionless manner. By contrast, certain other types of cartilage, which are present in non-articulating structures such as spinal discs, ears, noses, and windpipes, do not have articulating surfaces. Those types of cartilage are very different (both structurally and functionally) from hyaline and meniscal cartilage, and the design and implantation requirements that arise, when non-articulating cartilage segments are being repaired or replaced, are very different from the requirements that apply to implants that will be used to repair or replace hyaline or meniscal cartilage.

Accordingly, any references herein to "cartilage" are limited to articulating cartilage (i.e., to hyaline, meniscal, or labral cartilage), and any prior art devices which have been developed for repairing or replacing non-articulating cartilage (such as in windpipes, ears, or spinal discs) are regarded as not relevant to this invention, since the structural and functional requirements and constraints that arise in the repair of non-articulating cartilage are so different from articulating cartilage.

Because hyaline and meniscal cartilage segments do not have a normal blood supply, and because they are subjected to compressive and shearing forces and stresses whenever a joint is moved, it is very difficult and in most cases impossible for cartilage to heal and recover, if it becomes abraded, injured, diseased, or otherwise damaged. Therefore, a huge amount of effort has been devoted to developing implant devices that can be used to permanently replace segments of cartilage that have been damaged.

One set of efforts which require attention herein has been carried out by the Applicant herein, Kevin Mansmann, an orthopedic surgeon who works in Pennsylvania. As described and illustrated in a number of issued patents and published applications, Dr. Mansmann has been focusing on designing, developing, and testing cartilage-replacing implant devices that contain synthetic "hydrogel" polymers.

As suggested by the name, "hydrogel" polymers hold and contain water. In the types of polymers that are of interest herein, chemical reactions are used to convert "monomer" reagents into polymerized molecules which have long "backbone" chains, with specialized side groups that are bonded to the long backbone chains. The relatively short "side groups" can also be called pendant groups, short chains, or similar terms, and in some cases they form covalent "bridges" which will connect different backbone chains to each other. A wide variety and assortment of side groups can be incorporated into polymers, by proper selection and control of the monomer reagents that will be used to make a polymer, and the lengths, densities, and other features of the side groups will determine the physical and performance traits of any particular polymer formulation (such as, for example, whether a polymer is hydrophobic or hydrophilic; whether it is hard and rigid, or soft and pliable; and, whether it is dense and compacted, or porous and able to absorb and hold water).

Accordingly, the ability to select from a wide range of candidate monomer compounds, which can incorporate various types of "side" chains or groups into a final polymerized compound, enables technicians to create synthetic polymer compounds which can function as hydrogels that can contain nearly any level of water content that is of interest. The water content of a hydrogel polymer can be expressed as a percentage (based on either weight, or volume) which is occupied by water rather than polymer molecules. Since percentages measured by weight are easier to determine (i.e., by simply comparing the weights of water-saturated polymer segments, versus dehydrated polymer segments), weight percentages are used more commonly, to compare and define different versions and formulations of the types of polymers of interest herein.

Essentially all of the cartilage-replacing surgical implant devices that are being manufactured and sold today with polymeric components use relatively hard and dense plastics which do not contain water, and which are not "hydrogel" polymers. Most such implants use a polymer called "ultra-high-molecular-weight polyethylene" (abbreviated as UHMWPE), especially in any "load-bearing" joints that need repair, such as knees and hips. Since the presence of any internal water, in any polymer, will necessarily and unavoidably lead to reduced strength and durability of that polymer (compared to water-impermeable hard plastics), the desire of orthopedic implant companies to provide the strongest and most durable implant devices that can be designed and manufactured, using modern technology, has generally led those companies to select and use water-impermeable polymers, for implant devices designed for load-bearing joints such as knees and hips.

However, hydrogel polymers (i.e., polymers which will absorb and hold a significant quantity of water, within the molecular framework or lattice which forms a polymeric material) are becoming of substantial interest for implant devices designed to replace cartilage, because of two important reasons.

First, synthetic hydrogels have the potential to emulate natural cartilage, much more closely than the types of hard and dense polymers that are used for conventional knee or hip replacements. Natural cartilage is a hydrogel material; it contains a relatively high water content, and the ability of the water molecules to move, travel, and dynamically redistribute themselves, in response to changes in localized pressures or stresses within a lattice or matrix of collagen fibers that form cartilage, plays an important role in the ability of cartilage to perform in its normal and desirable manner, whenever a joint is being moved and used.

A second major potential advantage of hydrogel polymers, compared to hard plastics, is that hydrogels can be much more flexible than hard plastics. As a result, hydrogel components offer the potential for creating relatively large implant devices that can be rolled into a cylindrical shape, inserted into a joint via an arthroscopic insertion tube (which can have roughly the diameter of a finger or thumb), and then unrolled or otherwise expanded into a final desired shape, after the implant has reached the interior of the joint that is being repaired. That type of arthroscopic repair inflicts much less damage and disruption on the muscles, tendons, blood vessels, and other soft tissues that surround a joint, compared to the types of surgery used to insert implants with hard plastic and metal components, in conventional knee or hip replacements.

As a result, orthopedic implant companies continue to monitor any advances that are being made in the development of stronger and more durable hydrogel polymer materials. Those companies are fully aware that if hydrogel polymers can be made with sufficient levels of toughness and durability to last for decades, even in load-bearing joints such as knees or hips, implants containing those types of polymers could provide not just one but two major advantages: (1) the flexible implants that hydrogels can help create would enable various types of arthroscopic repair of damaged joints, which cannot be accomplished when non-flexible hard plastic components are used; and, (2) hydrogel-containing synthetic polymers can emulate natural collagen, more closely than can be accomplished by the hard and rigid plastics that are being used in cartilage-replacing implants today. Accordingly, the work being done by Mansmann, using certain types of flexible synthetic hydrogels that have unusually high levels of strength and durability, offers the potential to enable a complete hip or knee replacement, using entirely arthroscopic methods and devices.

Certain other not-yet-published patent applications filed by the same inventor herein disclose a design approach for flexible cartilage-replacing implants that contain hydrogel polymers, and which use flexible cables to enable improved anchoring of the implant devices. These types of flexible cables will be embedded within a molded flexible hydrogel polymer component, in a peripheral location which presumably (but not necessarily) creates a continuous loop that surrounds and encompasses the entire periphery of the implant device. One example of such an implant can be provided by an oval-shaped or otherwise elongated implant device that is designed to resurface (and to completely replace the native cartilage on) a femoral runner, on either the medial or lateral side (or compartment) of a femoral condyle, in a knee joint. This type of implant device can be molded in a manner which generates an enlarged peripheral component, referred to herein as an enlarged rim component. That enlarged rim component will be designed to fit, in an accommodating manner, into a groove which will be machined (with the aid of templates and/or a computer-controlled cutting or grinding tool) into a hard bone surface that is being prepared to receive and support the implant device.

After the native cartilage has been removed (by cutting, grinding, and suctioning) from a bone surface that is being surgically repaired, a groove having a controlled size and shape will be machined into the bone surface, in a location that generally surrounds and encompasses the area where the implant will be positioned. After that preparative work has been completed, the flexible implant device (which has been temporarily rolled into a cylindrical shape) will be inserted into the joint, via an arthroscopic insertion tube. Once inside the joint, the flexible implant will be unrolled to return it to its manufactured shape, and it will be secured to the bone. When the enlarged rim component of the implant settles into the peripheral groove that was machined into the bone surface, that engagement of two accommodating shaped surfaces will help secure and anchor the implant to the bone in a strong, stable, and secure manner that will be better able to resist compressive, lateral, and other types of forces and stresses that will be imposed on the implant when the knee, hip, or other joint is being used and moved by the person or animal.

Accordingly, a flexible anchoring cable, made of multiple strands of a high-strength polymer and/or a non-corroding biocompatible alloy, can be embedded within an enlarged peripheral rim structure, which will surround a flexible implant of the type described above. If that type of peripheral anchoring cable is embedded within the molded polymeric component of a flexible implant, then a set of suture strands, flexible wires, or similar components can be wrapped around the anchoring cable at a plurality of locations, and the suture strands or wires (which can have any desired length) will emerge from the molded polymeric device, at locations that are suitably spaced and positioned around the periphery of the implant device.

For purposes of discussion herein, it is assumed that the strands or wires that emerge from the molded polymeric component of the anchoring device will be in the form of a segment of braided cable, made of at least three and up to about ten relatively thin strands of material. Those strands presumably will be made of a high-strength biocompatible polymer, such as ultra-high-molecular weight polyethylene (UHMWPE), which is well known and widely used in connection with various types of surgical implants. For convenience, and to clearly distinguish these segments of braided cables from the main anchoring cable which is embedded within the implant device, these suture cable segments which emerge from the polymeric component of an implant device are referred to herein as braided suture segments (or strands), or simply as suture segments (or strands), for convenience.

Typically, both of the two ends of a braided suture segment will be "free" (typically with a length of several inches for each free segment), thereby making both ends readily accessible to a surgeon. The center portion of a suture segment will be wrapped around the anchoring cable segment that is embedded within the implant. That wrapping-type attachment preferably should use a plurality of "turns" of the suture strand, around the embedded cable, to reduce any risk of slippage or other relative motion of the suture strand inside the molded polymeric component.

This current patent application focuses primarily on the types of devices that can be used to secure, and adjust, the "free ends" of the suture strands that emerge from a polymeric component of a flexible cartilage-replacing implant. Those free ends will be attached, by the surgeon, to either hard bone or soft tissue in the vicinity of the implant, in a manner which will help stabilize and reinforce the implant.

When the Applicant herein began to consider and focus on the details of how a set of suture strands could be affixed to bone surfaces, to help anchor an implant device that would replace damaged cartilage in a joint such as a knee, his attention turned to knotless suture anchors. When he realized that none of the knotless anchor designs that are currently available would be optimal for the particular type of use he intended, he began to focus on how new and different types of knotless suture anchors could be designed, which would be optimized for that particular type of intended use.

Those analyses led him to conclude that a new design for "ratcheting" suture anchors can provide substantial improvements over all other currently known types of "ratcheting" or other suture anchors.

A full understanding of the preceding sentence will require some background information on ratchet mechanisms.

Rachet Mechanisms

Some sources assert that "ratchet" is the proper spelling for the mechanical components and systems discussed herein; however, other sources assert that "ratchet" is the proper spelling. Accordingly, both spellings should be regarded and accepted as alternate correct spellings.

In addition to having two different spellings, the term "ratchet" has acquired two different meanings Those different meanings can lead to confusion and conflict, if not fully understood.

A "classic" and relatively narrow definition of "ratchet", which normally would be used by specialists such as mechanical engineers, requires the presence of both a gear and a "pawl". This type of ratchet mechanism 20, which has been known for centuries in the prior art, is illustrated in a simplified form in FIG. 1, which is prior art, and which shows a rotating gear 22 having surface protrusions 24 (often called teeth, cogs, or similar terms). Under the classic and narrow definition, a ratcheting mechanism must also contain a "pawl" 26, which refers to any type of mechanism that will engage the teeth of the rotating gear in a manner that allows rotation in one direction, but not the other direction.

The designs of various types of interactive gears and pawls can become complex and sophisticated, and FIG. 1 is a simplified depiction of a basic mechanism. The pawl 26 is mounted on its own axle 27, and the operating end of pawl 26 is pressed against the teeth of gear 22 by the action of spring 28, which is mounted against a relatively stationary surface 29. The external spring is shown, solely for purposes of illustrating the basic arrangement; in nearly all types of pawl systems in use today, an internal (and therefore protected and unintrusive) coil spring is coupled to the axle of the pawl, to provide the same effect.

In a "classic" ratchet mechanism, the positioning and movement of the pawl constrains the travel of the gear, in a manner which allows the gear to rotate in only one direction. If a rotational force drives the gear to rotate in the direction shown by the block arrow in FIG. 1, the surface of gear tooth 24a will press against the side of pawl 26, in a way which will deflect pawl 26, causing it to rotate slightly about its axle 27 while spring 28 is compressed slightly. This allows gear tooth 24a to move "forward" and occupy the position currently occupied by tooth 24b in FIG. 1, which presses directly against the end of pawl 26.

A properly-designed pawl will not deflect and temporarily move out of the way, if the lower surface of gear tooth 24b presses against the end surface of pawl 26. In the depiction in FIG. 1, the axle-mounted placement of the pawl will allow the pawl to be deflected in a "sideways" (i.e., left-and-right)

manner, but it will not allow the upper end of pawl to move in a "downward" direction. This is comparable to saying that if a conventional wagon is sitting on a sidewalk, it can be pulled horizontally, with relatively little effort, and it will simply roll, because of how its wheels and axles function. However, that same wagon cannot be pressed downward, into the sidewalk, without damaging and effectively breaking the wagon.

Ratchet mechanisms of this type are common and well-known. If desired, they can be modified in various ways, to adapt them for additional purposes. For example, in a so-called "ratchet wrench" (or ratcheting screwdriver), a V-shaped pawl with two arms can be mounted next to a gear, using an axle component that will allow either one arm of the pawl, or the other arm of the pawl, to engage the toothed gear at any particular time. In this way, operation of an external lever or other control device will allow the user of a ratchet wrench (or screwdriver) to set the tool in a first configuration that will tighten a bolt, nut, or screw when desired, and to subsequently change the setting of the wrench or screwdriver, so that it can loosen a bolt, nut, or screw.

Alternately, a ratchet wrench or screwdriver can have two separate and independent pawl components, and an external control lever will rotate an internal component which can push either pawl out of engagement with the gear, while allowing the other pawl to move into contact with the gear and engage it.

Accordingly, in the relatively narrow "classic" definition, a true "ratchet" system requires a gear, and at least one pawl component which can engage and constrain the gear in a manner that allows the gear to rotate in only one direction for as long as the pawl engages the gear.

However, a broader definition has emerged, which is widely and commonly used, and which is preferred and used herein. Since most users do not know or care what type of mechanism is being used to create a ratcheting effect, the term "ratchet" has come to include any mechanical linkage which allows motion in one direction (which can be linear, rotational, or any combination), while preventing motion in the "other" direction (which can also be called the opposite, prohibited, blocked, or non-allowed direction, or similar terms).

Yet another uncertainty can arise, in determining whether the term "ratchet" should:

(1) be strictly and narrowly limited, so that it applies only to devices and systems having mechanisms which completely block and prohibit motion in a "non-allowed" direction; or, (2) be used in a more expansive and tolerant manner, to also include devices which can impede (or "strongly impede") motion in a non-allowed direction, at a level which is sufficient to generally prevent such motion.

The types and classes of mechanisms which dwell in that zone of uncertainty, where it is not clear whether they do or do not properly and accurately qualify as "ratchet" devices or system, is illustrated and exemplified by the type of belt buckle that is often called a "cinch buckle". This type of buckle, which is often found on woven or braided belts that are used to hold up trousers (cinch buckles normally are not used with leather belts or straps, since they would damage the leather), involves two metallic rings which are adjacent or close to each other, where they effectively become "parallel" circles or arcs. Each metal ring will have a portion (which can be a straight segment, within an otherwise circular ring) that is constrained within the webbing or fabric of the belt. When the free end of a belt is looped through a "cinch buckle", the act of looping the belt over and around the "top" ring, before lacing it back through the lower ring and then pulling it tight (so that the rough or textured surface of a woven or braided belt will be pressed against itself) creates a squeezing and crimping force which pulls and presses the upper ring (and its loop of belt material) downward against the lower ring. In this manner, the two adjacent metal rings can squeeze and effectively grab a woven or braided belt, with sufficient strength to allow the belt to function adequately, in holding up trousers.

Accordingly, a cinch buckle can qualify as a ratcheting device, under a broad definition of "ratchet", since it allows one end of a belt or strap to be pulled in one direction (i.e., in a tightening direction), and it then generally prevents that end of the belt or strap from traveling in the opposite direction (which would quickly loosen the belt or strap).

However, the fact that a cinch buckle can only generally prevent travel of a belt or strap in a non-allowed direction requires attention, because a cinch buckle does not have any mechanism which truly prevents and prohibits such travel (which is often referred to by terms such as slippage, creep, etc.). In general, a belt with a cinch buckle is adequate for holding up trousers, only if the person wearing the belt is able to conveniently and discretely reach down and tighten the belt when necessary to do so, during the course of a day or evening, each time the belt becomes too loose to function effectively. If desired, the surfaces of the rings can be have knurled or other rough or textured surfaces, which can help reduce slippage, but those types of steps do not change the nature of a cinch buckle.

To a large extent, the proper use of terms such as "ratchet" will depend on the setting, functional requirements, and context of the usage. For example, a cinch buckle might properly and reasonably be referred to as a ratchet mechanism, if used to secure a belt around a duffel bag or comparable item that is being used to store or transport clothes or other lightweight items.

However, a cinch buckle cannot be used to safely secure heavy cargo to a flatbed trailer, in the types of 18-wheeler trucks that haul cargo across highways. Since the risk of a cinch buckle gradually losing its "grip" on a strap or belt is so high, in an environment where vibration, jostling, or other repetitive motion occurs (and where unintended release of the cargo, from a truck driving at high speed down a highway) might kill or maim innocent people, it would constitute reckless disregard and even criminal neglect if a trucking company used "cinch buckles" on nylon straps to secure heavy cargo to truck trailers. Accordingly, in that type of setting, a cinch buckle should not be referred to as a ratchet mechanism.

Before moving on to a class of ratchet devices called "cam cleats", it also should be noted that various types of ratcheting systems, devices, and designs are known, where it is not clear whether some particular mechanism does, or does not, comprise a gear-and-pawl system. As one example, in various types of devices (such as child-proof caps on pill bottles, in the lids of plastic pails that hold chemicals for swimming pools, etc.), a cylinder, disc, cap, or other rotatable component can be provided with a protruding "flap" or ramp-like structure on its periphery. When provided on the cap or lid of a container, that ramp-like structure usually is designed to rub against (and move across) a series of accommodating slots or ridges, which have been molded into the neck of the bottle, jar, pail, or other portion of the container, when the cap or lid is being tightened. Subsequently, if someone tries to remove the cap or lid, by rotating it in the opposite direction, the ramped structure on the cap or lid will "catch" on the slots or ridges of the bottle or pail, in a manner which will prevent rotation, unless certain additional steps are taken. Accordingly, this type of "safety" cap or lid can prevent a toddler from opening a bottle of pills, and it can prevent a pail of chemicals from coming open accidentally.

The point that should be recognized, in analyzing what might or might not qualify as a "true" or "classic" ratchet, is that some mechanical engineers would label the protruding component on such a cap or lid as a "pawl", and would label the ridged or slotted components on the container as a "gear" (or gears), but other mechanical engineers likely would not agree that those "classic" terms should be stretched far enough to cover those types of devices.

Similarly, in the system illustrated in US application 2010/0063542 (Van Der Burg et al), a pin, which projects outwardly from a rotating internal component, interacts with a sawtooth surface on top of a cylindrical sleeve which surrounds the internal member (similar systems are widely used in retractable ballpoint pens, to allow an endless number of extensions and retractions of the ink point, by repeatedly pressing a button-type device mounted on top of the barrel of the pen). Some mechanical engineers might regard Van Der Burg's pin mechanism as a "classic" gear-and-pawl system, while others probably would not.

As shown by the various examples above, the narrow definition of "ratchet" systems (i.e., as being limited to "gear and pawl" systems) is not merely limiting, it is uncertain, potentially confusing, and difficult to apply and use consistently, when one realizes how many borderline cases might or might not be covered by the narrowly-defined "classic" definition. Therefore, the broader definition (i.e., to include any mechanical mechanism that is designed to allow travel of some component in one direction, while generally prohibiting and preventing travel of that component in the opposite direction) is clearer, and makes better logical and practical sense, and is preferred and used herein.

One example of ratchet linkages other than the classic "gear and pawl" linkage is provided by devices called "cam cleats", which are commonly used on sailboats to temporarily secure ropes in certain positions. A cam cleat is generally depicted in FIG. 2, and better illustrations (including photographs of actual devices) are readily available in the online catalogs of companies that sell sailboat equipment.

The term "cleat" has been used for centuries, to refer to certain types of devices which are mounted on sailboat rails, and on docks, piers, and similar locations. Cleats are designed to enable ropes to be secured to them, without requiring a rope to be tied into a knot; alternately, if a knot is used to create a loop at the end of a rope, then that loop will effectively become a permanent part of that rope, and the knot will not need to be tied, and then untied, for each "cycle" of use.

There are powerful reasons, in sailing, for not wanting to have to repeatedly tie and untie knots in ropes. When large pulling forces are exerted on any knot (as often occurs whenever boats are involved, due to waves, tides, wakes from other boats, etc.), a knot that has been subjected to even a single moment of a large tensile force can be compacted into a very tight and hard configuration. It can be very difficult (or effectively impossible) to untie a knot which has been tightened to an extreme level of tightness and hardness, without tedious and extensive effort. Therefore, "cleats" were developed and designed as mechanisms that allow ropes to be secured to them, without requiring those ropes to be tied into knots.

In mechanical terms, "cam" refers to devices which generate some type of linear motion or travel when they rotate. This is usually accomplished by either of two types of designs. In one design, a gear or similar rotatable component (which might have either a smooth surface, or a toothed, textured, or other non-smooth surface), which has a genuinely circular shape, is affixed to a rotating axle, in some location other than the center of the gear. This creates an "eccentric" mounting of the gear, on the axle. As a result, each time the gear rotates through a complete revolution, while the axle is held in a constrained position, the "apparent" surface (or thickness) of the gear, when viewed from some particular angle, will generate a reciprocating (i.e., back-and-forth) linear motion, which can be imparted to a device such as a spring-mounted linear component.

The other main type of design for cam devices uses a rotating shape which is not truly circular. An example is provided by the "camshaft" devices used by automobile engines. A typical "cam gear" of this type has roughly the same elongated shape of a chicken egg, so that each time the camshaft rotates through a cycle, the "point" of each cam gear mounted on the camshaft will cause an engine valve to be displaced slightly, in a manner that will briefly open that particular engine valve. The inlet valves allow fuel or oxygen to enter a cylinder, in a manner that is precisely timed and controlled by rotation of the numerous non-circular gears on the camshaft, while the outlet valves allow the hot exhaust gases to exit the cylinders, at carefully synchronized moments in time.

Regardless of which type of design is used, cam devices are designed to cause "translational" (linear) motion of a surface which can rotate about an axle. Some cam devices make complete and multiple rotations (such as automobile camshafts), while other types of cam devices never complete a full rotational cycle.

A typical cam cleat, on a sailboat, has two gears, and neither gear is able to rotate through an entire circle. As indicated by the cam cleat mechanism 40, as shown in FIG. 2 (which is prior art), the two gears 42 and 44 are mounted on axle components 42*a* and 44*a*. Each axle incorporates a spring-loaded mechanism, to constantly exert a low-level force on each of the gears 42 and 44, which will constantly try to close the two gears together. The spring-generated force which attempts to close the two gears against each other will ensure that the ridges or "teeth" 42*b* and 44*b* of the two gears 42 and 44 will continually be pressed against the surface of rope 49, which passes between the two gears.

For simplicity of illustration, the surfaces of rope 49 are shown as being smooth. In practice, any such rope (usually braided from multiple strands of nylon or polypropylene) will have a rough or textured surface, which will enable a better "grip" by a cam cleat. A "monofilament" rope (as used in fishing lines, to make it harder for fish to see a line attached to a lure or bait) would not be used in this type of setting.

Because of the design and arrangement of cam cleat 40, as illustrated in FIG. 2, rope 49 can be pulled through cam cleat 40 in only one direction, shown by the block arrow, with little or no resistance. However, if the rope tries to travel in the opposite direction, through the cam cleat, the teeth 42*b* and 44*b* on the non-circular cammed surfaces of the two gears 42 and 44 will "bite into" the rope, in a manner which prevents travel of the rope in the "blocked" or prohibited direction. As the teeth on the two gears 42 and 44 rotate slightly in the "not allowed" direction, due to a pulling action exerted by the surface of the rope, the ridges of those surfaces will be pulled closer together, because of the non-circular cammed shape of gears 42 and 44. This will cause the gear teeth to "bite" even harder into the rope. This generates a powerful squeezing and gripping force, and if the rope is pulled even harder, the gears of the cam cleat will be pulled even closer together, causing the cleat to grip the rope even more tightly than before.

In a typical cam cleat on a sailboat, the cam cleat will have either: (1) an open top surface, to allow someone to quickly release the rope from the cleat, by jerking the rope in an upward direction, at a location near the cleat; or, (2) a specialized constraining bracket, which will require the rope to be pulled upward in a specific manner, before the rope will be released by the two cam gears. That type of constraining bracket can reduce the risk of accidental release of a rope at an unwanted and possibly dangerous time.

The risk of accidental release of a rope, by a cam cleat, merits attention. In general, on sailboats, cam cleats without adjacent fixed cleats are used only for temporarily securing ropes that are called "sheets". This set of ropes is used to trim the sails (i.e. they are used to pull sails and booms in horizontal directions). By contrast, any ropes that are used to raise or lower sails or booms (or other devices), in a vertical direction, are referred to as "halyards". The distinction between "sheets" and "halyards" is crucially important, and it is taught in any beginning class on sailing.

Halyards are not used nearly as frequently as sheets, and a sudden failure of a halyard would be more likely to cause a serious and perhaps catastrophic problem or failure, up to and including sinking of a boat, and loss of life. Therefore, if a cam cleat is included in the mechanism that is used to raise a halyard on a small sailboat, a fixed cleat can be positioned next to the cam cleat. This arrangement will allow a sailor to get a secure grip on a halyard, pull hard on it to raise a sail a limited distance, and then let go of the halyard for a moment, in order to grab the halyard at a spot closer to the mast, to provide a better grip and better leverage for the next tug on the rope. Accordingly, the type of ratcheting control that is provided by a cam cleat allows someone to raise a sail all the way up a mast, by means of a series of short pulls on a halyard rope. Once the sail has been raised, the halyard is secured to a fixed cleat mounted next to the cam cleat, to ensure that the rope cannot be released accidentally.

Alternately, a sailor on a small sailboat can simply wrap the free end of a halyard rope around the mast, and lightly tie the rope to the mast, using a simple knot. The act of securing the rope close to the mast will effectively cause the rope to remain near the bottom of the cam cleat gears, and will help ensure that the rope will not be lifted and raised, somehow, out of the grip of the gears in the cam cleat.

In contrast to halyards, which raise and lower things vertically on a boat, cam cleats are frequently used to pull and secure "sheet" ropes on a sailboat, despite the well-known and well-recognized risks that cam cleats (especially "open top" cam cleats) sometimes fail. Skilled sailors must learn to accept and respect those risks; for example, if they hear a suspicious sound which indicates that something might be going wrong, they are taught to duck, immediately, rather than stand up and look around, in case a cam-cleat has failed and has allowed a fast-moving boom to swing around unexpectedly. There are plenty of references to sailors "taking swimming lessons" if they fail to recognize and respect the risk that a cam cleat might fail and release a rope it was holding.

Other types of mechanical ratcheting systems are also known. For example, some types of cam cleats have a single non-circular gear which can rotate; when the rope attempts to pull that gear in the non-allowed direction, the teeth on the non-circular gear will press the rope harder and harder into a constrained channel which has non-moving but ridged gripping surfaces. These types of single-gear cam cleats can be found on adjustable bungee cords and various other devices.

Advantages of Racheting Anchors for Securing Cartilage Implants; Start-Snug-Tighten Procedures When used to help anchor and reinforce surgical implants that are designed to replace damaged cartilage, one of the advantages that could be provided by ratcheting suture anchors—if such devices are developed and manufactured with sufficiently high levels of reliability, and sufficiently low risks and rates of failure—is that they would enable a surgeon to perform a type of installation procedure that would be very useful.

Those three steps can be summarized in the phrase, "start them all, then snug them all, then tighten them all".

If desired, that phrase can be shortened to "start, snug, tighten", so long as the reader understands that the entire "start" procedure must be finished for all of the sutures, before the second procedure should be started for any of the sutures. If each anchoring suture strand in a multi-strand system can progress through all three of the "start, snug, tighten" steps in a coordinated manner, then a single surgeon can perform an anchoring procedure that otherwise might require two or more people to achieve.

An example of how this type of approach can work, in a completely different field, involves replacing a flat tire, on a typical passenger automobile. After the car has been jacked up to remove the weight from the flat tire, the wheel (i.e., the steel or alloy "hub" component), with the tire that has gone flat still affixed to the wheel, is pulled off of an assembly (usually called the "wheel mount") which remains affixed to the car. A replacement wheel which carries a properly inflated tire must then be mounted, on the wheel mount.

In nearly all modern passenger cars, the wheel mount will have either four or five "studs" (i.e., threaded bolts) which protrude out from the wheel mount. Those studs will fit into accommodating holes on a wheel which is carried in the car, as a spare. The use of protruding studs on a wheel mount (rather than threaded holes, recessed into the wheel mount) allows any person who is replacing the wheel to lift the new wheel and tire slightly and place them onto the wheel mount, in a first step that does not involve any lug nuts. This makes it much easier to position a spare tire on a wheel mount, than would be required if a person had to hold a wheel and tire at an exact stationary height, while also struggling to get the end of a bolt inserted and then properly seated and started, in a recessed threaded hole.

Once the new wheel with the spare tire is in place, with all four or five studs passing through accommodating holes in the wheel, it is not good practice to screw on and then fully tighten a first lug nut, and then screw on and fully tighten a second lug nut, and then a third, and fourth, etc. Instead, each and every one of the lug nuts should progress through a "start them all, then snug them all, then tighten them all" routine, by the person replacing the flat tire.

In this context, "start" refers to getting each threaded lug nuts properly started on a threaded stud, with the threads of the nut and the stud properly engaged with each other, so that it will not damage either the nut or the stud, when the nut is forcibly screwed onto the stud.

After all four (or five) of the lug nuts have been fully and properly "started" on the studs, the next step is to get all four (or five) lug nuts properly "snugged". This term refers to a process in which the fingers (and possibly a wrench, using low force) are used to screw the nuts farther onto the studs, until a beveled or rounded surface on the inner side of each lug nut has become properly "seated" against the corresponding beveled or rounded surface of a hole in the wheel. That "snugging" step cannot and will not be accomplished in a secure and reliable manner, if the operator: (i) fully tightens a first lug nut, while all of the other lug nuts remain loose; and then, (ii) fully tightens a second lug nut, while the remaining lug nuts remain loose; and then, (iii) fully tightens a third lug nut, etc.

Instead, the process of properly "seating" and securing the entire wheel-and-tire assembly, to the wheel mount, is crucially important. That process can be accomplished, with much higher levels of safety and security, by "snugging" all of the nuts against the wheel holes, before any of the nuts are fully tightened.

Finally, after all lug nuts have been fully "snugged", with a modest but substantial level of tightness to ensure that the entire wheel has been properly "seated" on the wheel mount, the best way to fully tighten the lug nuts is by using a "bracketing" or "opposites" sequence. As soon as a first lug nut has been fully tightened, the next lug nut which should be tightened should be on the opposite side of the wheel (or as close to opposite as possible, if the wheel has five holes). By doing the first two tightening operations on two lug nuts which are as far apart from each other as possible, a person replacing a flat tire can make sure there is no "last second settling" or other shifting, pulling, or other motion which might raise questions about whether the new wheel is fully and properly seated on the wheel mount.

Accordingly, the entire process can be summarized as "start them all, then snug them all, then tighten them all"; or, in even shorter form, that entire sequence can be referred to as, "start, snug, tighten", so long as a listener or reader understands the full sequence.

Returning to the subject of suture anchors used during surgery, if knotless suture anchors with ratcheting mechanisms can be developed and mass-manufactured with sufficiently high levels of reliability and safety (which will require very low or non-existent failure rates), then those types of ratcheting anchors can enable a directly comparable "start, then snug, then tighten" installation procedure, for use with relatively large cartilage-replacing implants. Each and all of the multiple suture strands which will be used, to help securely anchor a cartilage-replacing implant to a bone, can and should go through a "start, then snug, then tighten" cycle of steps.

In this type of procedure, each and all of the suture anchors that will be used to help anchor an implant to a bone, in a load-bearing joint such as a knee, should be properly "started" (i.e., emplaced into the supporting bone) before any of the suture strands are pulled "snug", since any prematurely "snug" strand might distort or misalign a flexible implant, or otherwise render it more difficult for the surgeon to emplace all of the anchors in truly optimal positions.

After all of the anchors and strands have been "started", they should all be "snugged", in a manner which will provide gentle yet reliable assurance that the implant has become fully seated in its final desired position on the bone, with no unwanted distortions caused by any particular anchoring strand.

After all of the anchoring strands have been properly tensioned to a balanced and symmetric level of "snugness" around the full periphery of the implant, the final tightening steps should be carried out, preferably in a sequence that preserves a properly balanced load distribution, by initial selection and tightening of suture strands that are positioned on opposing or "bracketing" sides or ends of the implant.

Once that type of installing, anchoring, and reinforcing procedure is understood, and after certain types of candidate ratchet mechanisms have been explained and illustrated, then certain advantages, benefits, and improvements that can be provided the ratcheting system disclosed herein, compared to the prior ratcheting system disclosed in the two Van der Burg applications, will begin to become clear. Those advantages will be discussed below, after the mechanisms themselves have been explained and illustrated.

Accordingly, one object of this invention is to disclose one or more ratcheting mechanisms, for incorporation into knotless suture anchors, which will provide sufficiently high levels of security, stability, and reliability to justify and enable their use in surgical implantation of surgical implants that contain specialized surfaces which promote tissue ingrowth, for stronger and more stable anchoring purposes, over a span of weeks or months.

Another object of this invention is to disclose and provide methods for improved anchoring of surgical implants that contain tissue-ingrowth surfaces, using a combination of: (i) suture segments which emerge from such implants, and (ii) knotless ratcheting-type suture anchors as described herein, which are designed to allow surgeons to tension and tighten, in a staged, sequential, and controlled manner, each of the suture segments that emerge from various locations around the periphery of an implant.

Another object of this invention is to disclose designs which are believed to be novel, for knotless suture anchors that have ratcheting mechanisms which will allow surgeons to tension and tighten, in a staged, sequential, and controlled manner, each of a number of suture segments that will be used to anchor and reinforce a surgical implant device, especially among implant devices that contain surfaces which promote tissue ingrowth.

These and other objects of the invention will become more apparent through the following summary, drawings, and detailed description.

SUMMARY OF THE INVENTION

Miniaturized devices are disclosed that will provide knotless anchors for use in combination with suture strands, for anchoring surgical implants (such as implants that will replace damaged cartilage) in a joint, limb, or body of a patient. These knotless suture anchors will contain one or more types of ratcheting mechanisms, to allow a surgeon to pull a suture strand through an anchor device in one direction, without allowing the suture strand to travel or creep backward, in the other direction. This will allow a surgeon to emplace a number of such anchors in hard bone(s) or soft tissue(s), during installation of an implant, while the various suture strands remain loose and do not interfere with proper positioning of the implant. When the implant device is roughly in position, the surgeon can gently "snug" all of the suture strands (which preferably should be braided, to provide a non-smooth surface that will enable a stronger and more secure grip by the ratcheting mechanism), so that they will all reach a moderate plateau of gentle yet firm tension. After the surgeon has ensured that the implant is in proper position, with all of the anchoring sutures in a "snug" status, a series of final tightening and tensioning steps can be carried out on all of the suture strands. Accordingly, this sequence (i.e., start them all, then snug them all, then tighten them all) will ensure that all of the anchoring sutures are properly secured in a coordinated and balanced manner, to help ensure that a surgical implant is installed into its exact intended position.

In addition, unlike a rotating ratchet mechanism which must be driven by some type of wrench or other tool, all ratchet mechanisms disclosed herein allow an anchoring suture to pass entirely through its ratcheting anchor device, in a manner that will provide a "free end" of the suture strand which can be grasped by a surgeon (normally with the aid of minimally-invasive tools, comparable to needle-nose pliers) and pulled to any desired level of tension and tightness. This can preserve a normal and natural "feel", which will allow a surgeon to directly feel and monitor the progress of the tightening steps for each anchoring suture.

When used with implants that are affixed directly to a bone surface, to replace damaged hyaline cartilage on bone condyles, the reinforcement provided by the suture strands will be gradually supplanted and rendered unnecessary, over a span of weeks or months, as bony tissue grows into a porous anchoring layer on the bone-contacting anchoring surface of the implant.

It also should be noted that these types of ratcheting suture anchors, while initially developed and intended for use in anchoring and reinforcing cartilage-replacing implants, also can be adapted for other uses as well, such as for repairing torn rotator cuffs in shoulder joints.

BRIEF DESCRIPTION OF THE DRAWINGS

FIG. 3 depicts: (i) an anchoring cable which will be embedded within a surgical implant that is sized and designed to replace the cartilage of a femoral runner in a human knee joint; and, (ii) four braided suture segments which have their center portions wrapped around the anchoring cable at spaced locations, thereby generating suture segments having free ends which pass through a ratcheting suture anchor designed to be embedded in a hard bone.

FIG. 4 depicts the same anchoring cable and suture segments shown in FIG. 1, where the anchoring cable is embedded within a polymeric hydrogel component, while the free ends of the suture segments emerge from the surface of the polymer component.

DETAILED DESCRIPTION

Figure 1:
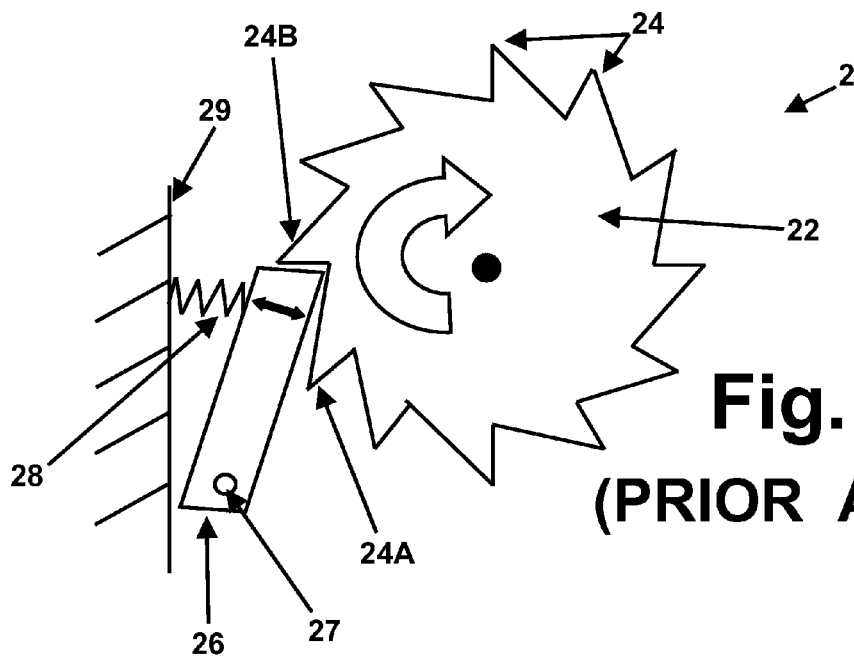
FIG. 1 (which is prior art) depicts a "classic" ratchet system, with a gear that is constrained by a spring-mounted pawl in a manner which allows the gear to rotate in only one direction.

As summarized above, this invention involves surgical implant devices, including but not limited to flexible devices that can be used in arthroscopic or other minimally-invasive surgery to replace damaged cartilage in articulating joints. One aspect of this invention involves knotless suture anchors that contain ratcheting mechanisms, which can be manufactured and sold, independently, for use in conjunction with various types of surgical implants that are sized, designed, and suited for either human or veterinary use.

Another aspect of this invention involves complete implant assemblies, wherein a complete assembly will include the implant device along with a plurality of ratcheting suture anchors which are affixed to suture strands that will be used to help install, anchor, and reinforce the implant device.

One particular class of implant device assemblies which can benefit from this design includes flexible implant devices that can be inserted into articulating joints or other body parts using arthroscopic or other minimally-invasive methods.

The types of ratcheting mechanisms which can be provided within these types of knotless suture anchors will allow a surgeon to pull a suture strand (which preferably should be braided, to provide a non-smooth surface that will give a ratcheting mechanism a stronger and more secure grip on the suture strand) through a ratcheting anchor in one direction only. This will allow a surgeon to emplace a number of such anchors in hard bone or other tissue, during installation of an implant, while the various suture strands remain loose, so that they will not interfere with proper positioning of the implant. When the implant device is roughly in position, the surgeon can gently "snug" all of the suture strands, so that they will all reach a moderate level of gentle tension in a balanced and symmetric manner, without distorting or disrupting the positioning and seating of the implant. After the surgeon has ensured that the implant remains in proper position after all of the anchored sutures are snug, a series of final tightening and tensioning steps can be carried out, on all of the suture strands, to ensure that all of them are properly tightened to a final desired tension in a coordinated and balanced manner, while the implant remains in its desired final position. This sequence of steps is referred to herein as, "start them all, snug them all, then tighten them all", or in condensed form as a "start, snug, tighten" procedure.

When used with implants that are affixed directly to a bone surface, such as to replace damaged hyaline cartilage on bone condyles, the reinforcement provided by the suture strands will be gradually supplanted and rendered unnecessary, over a span of months, as bony tissue grows into a porous anchoring layer on the bone-contacting anchoring surface of the implant. This factor, when combined with other design features of an implant as described herein, can overcome concerns about whether a ratcheting suture anchor might fail after a period of months, years, or even decades after an implant was surgically installed.

If desired, additional steps can be taken to help ensure that the ratcheting-type grip of a suture anchor on a suture strand will not slip or fail, after installation. One such step involves placing a drop of bone cement onto a ratcheting suture anchor, after any suture strands which pass through the anchor have been fully tightened, during installation of an implant. The bone cement (methylmethacrylate cements are well known and commonly used for bone surgery) will cure, harden, and set into a hard solid material, which will effectively freeze, immobilize, and lock the suture strand within the ratcheting suture anchor.

Alternately or additionally, a surgical staple or drop of glue can be used to effectively pin down the free end of a suture strand, somewhere close to a ratcheting suture anchor. Using this type of constraint can help ensure that a suture strand does not "work its way out" of the grip of a ratcheting mechanism. By way of analogy, if a sailor pulls a halyard rope through a cam cleat mounted on a mast, and then wraps the end of the rope around the mast and lightly ties the free end of the rope to the mast, the simple act of securing the rope close to the mast can ensure that the rope will not escape from the grip of the cam cleat.

As a third option, a surgeon can affix a clip or clasp to the "free end" of a suture strand, immediately adjacent to a ratcheting anchor, once the suture strand has been fully tightened Any decisions as to whether any "additional safeguards" are warranted, for any particular patient, will be made by a qualified surgeon at the time an implant is installed, and such decisions will be based on the surgeon's appraisal of the patient's age, condition, activity levels, and other factors. For example, if a knee repair is being performed on a man or woman who is more than 70 years old and who is not athletically active, a surgeon might well decide that additional safeguards are not required; by contrast, if a knee repair is being done on a young person or athlete who suffered an injury, the long-term goals will be substantially different, and a surgeon might decide to take every possible precaution to ensure the strongest possible strength and durability for the implant, over a span of multiple decades.

Figure 2:
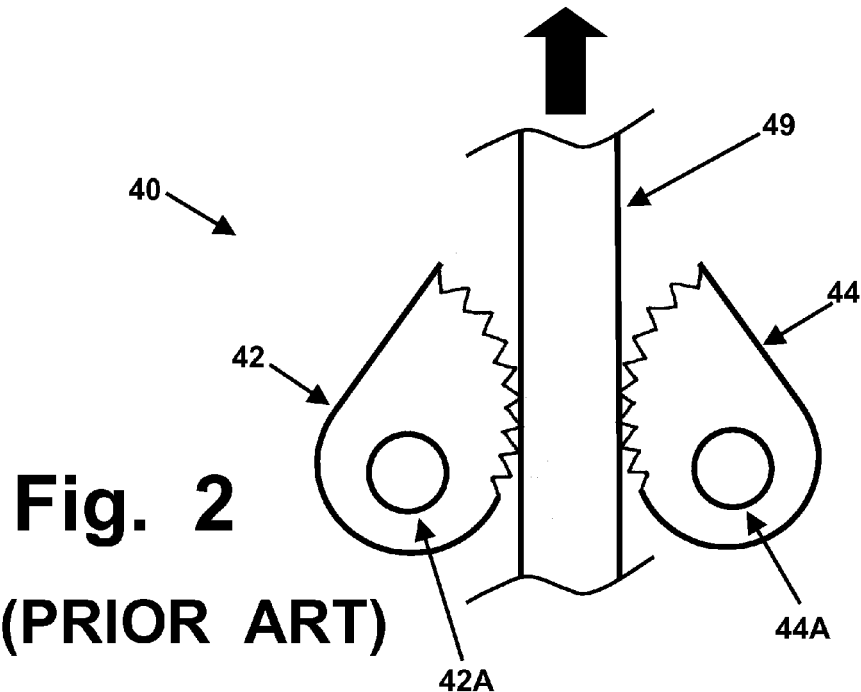
FIG. 2 (which is prior art) depicts the type of cam cleat that is used to secure a rope on a sailboat.

Referring to the figures, FIGS. 1 and 2 depict prior art, which was described in the Background section.

FIG. 3 depicts an anchoring assembly 100, which will be partially embedded within a flexible surgical implant 200, as depicted in FIG. 4. Anchoring assembly 100 comprises a twisted or braided cable component 110, which can be referred to as an anchoring cable, a peripheral cable, a main cable, or similar terms. This cable component 110 has been formed into a continuous loop, with the aid of an attachment collar 112 which grips and secures the two ends of the cable segment that was used to form the loop. Any suitable means can be used to form the cable into a continuous loop; for example, a chemical or heated fusing process can be performed on strands made of a polymer such as nylon or polyethylene, spot-welding can be used to fuse the ends of a cable made of a metal alloy, etc.

For purposes of illustration and description, the cable segment 110 shown in FIG. 3, and the flexible implant 200 shown in FIG. 4, are both sized and shaped to render them suitable for replacing a segment of damaged cartilage that covers a femoral runner. The femur is the long bone inside a patient's thigh, and each femur has two rounded "runners" (designed as the medial (inside) and lateral (outside) runners), which form part of a knee joint. The cartilage which covers the two femoral runner surfaces will press, rub, and slide against both: (i) the tibial plateau, which is the uppermost surface of the shinbone, and (ii) the interior surface of the patella (kneecap), which has two rounded concave surfaces which fit and slide against the two parallel femoral runners, in a manner which helps to stabilize the knee and prevent unwanted lateral motion between the bones in a knee joint.

The hyaline cartilage segments which cover femoral runners in knee joints often become abraded, injured, or otherwise damaged, and femoral cartilage replacement is a common type of knee surgery. Since those cartilage segments have exact sizes which can be readily measured and determined for any particular patient before the day of surgery (using X-rays or other diagnostic imaging), an orthopedic supply company can manufacture an assortment of implants having a range of sizes, which will be packaged as kits (which can also contain any accompanying supplies), in sealed packaging which maintains the sterility of the implants and supplies. A surgeon can select and order, in advance, a kit containing a femoral runner implant with the appropriate size for a particular patient, so that the kit and the implant will be available and ready, for that patient, on the day of surgery. If both of the two femoral runners in a knee joint (i.e., the medial runner, and the lateral runner) will be replaced in a single surgery (this type of surgery, called a bicompartment repair, is fairly common), the surgeon can order two kits, with one runner implant in each kit, or a single kit containing two runner implants if those are made available.

Returning to FIG. 3, the anchoring cable 110 has a number of suture strands (which can also be called anchoring strands or similar terms), designated by callout numbers 114 (for strands which pass individually through a suture anchor) or 116 (if two strands pass through a single suture anchor).

The pairing of two strands, which will pass through a single knotless suture anchor, has become a common design and practice, in orthopedic surgery. The use of a single anchoring device to secure two suture strands can reduce the risk of failure, for at least two reasons. First, nearly any type of knotless suture anchor will require one or more moving parts to create a clamping mechanism, and the clamping action poses some risk of creating shearing stresses, which might cut through a strand. Accordingly, the placement of two suture strands, immediately adjacent to each other, provides a type of padding for each of the two suture strands, and that padding can help both strands resist any shearing forces or damage. Secondly, if one of the two suture strands does fail, due to shearing damage from a clamping mechanism or any other reason, the other strand will still have a fairly high likelihood of maintaining its integrity, and under normal conditions, it will still be able to provide all the tensile strength that is required for that particular anchor.

Accordingly, single-strand anchors 120 and double-strand anchors 122 are both illustrated in FIGS. 3 and 4, even though conventional design and practice is to use either one approach, or the other, for all suture-anchor subassemblies in any particular implant.

It also should be noted that all of the suture strands 112 and 114 that are illustrated in FIGS. 3 and 4 are attached to locations which can be referred to as the "rounded corners" of femoral runner implant 100. In general, whenever a cartilage-replacing implant has a portion or location which, because of its shape, placement, or other factors, might pose a relatively high risk of being dislodged or "pried away" from a supporting bone (especially during a fall or other accident, when abnormally high instantaneous stresses might be imposed on the implant), then any such corner or vulnerable site becomes a candidate location for one or more anchoring sutures, to reinforce that particular corner or other portion of the implant.

This does not assert or imply that no other anchoring sutures should also be attached to a main anchoring cable, at other locations. For example, in a curved femoral runner implant, as illustrated in FIG. 4, it is likely that at least one or more additional anchoring sutures would be coupled to each of the side edges of the implant, to help ensure that those side edges are adequately secured to the curved bone surface, along the entire lengths of the side edges. However, to keep the illustrations relatively simple and clear, the only anchoring strands illustrated in FIGS. 3 and 4 are located on the rounded corners of the implant 100.

The suture strands 112 and 114 will be affixed to main anchoring cable 110 during a manufacturing operation, rather than during surgical implantation. Accordingly, any suitable attachment mode can be used to attach or couple the strands to the cable. In FIG. 3, each strand is shown as wrapped around the cable, with a plurality of windings (or turns, etc.). The use of multiple turns, which will be embedded within a high-strength molded polymer, can provide greater strength and stability, to help ensure that a strand will not suffer a displacement or shifting of the strand along the length of the cable (which could damage the implant, or jeopardize the strength of its anchoring), even if high peak stresses are imposed on the implant due to a fall or accident.

In addition, if a number of windings or turns with suitable "pitch" and displacement for each winding are used to create a significant distance between the locations where the two ends of a strand emerge from the polymer component of an implant, then the two emergent sites can function as two separate and distinct reinforcement sites along the periphery of the implant, for improved anchoring.

FIGS. 5 through 9 depict several different ratcheting mechanisms, all of which provide candidate mechanisms for incorporation into ratcheting knotless suture anchors. Using no more than routine experimentation, any orthopedic supply company can test and evaluate each of these candidate mechanisms, to determine which one will provide the best combination of strength, security, and reliability with any particular type of braided suture strand that is being evaluated for possible use as described herein. It is not asserted herein that any particular ratcheting mechanism will be preferred for use with all types and sizes of braided suture strands; instead, in the same way that multiple types of suture strands (made of different materials, and having different thicknesses and performance traits) are readily available to surgeons for a range of different uses, it is presumed and believed that an assortment of braided suture cables having a range of different thicknesses, flexibility, surface "tackiness", and other features will emerge over time, and will be preferred by various surgeons for use in anchoring different types of implants, or in other types of surgery, such as rotator cuff repairs. As just one illustration of that principle, it is very likely that the types of anchoring sutures which will become preferred for repairing finger joints will be thinner, lighter, and more flexible than anchoring sutures which will become preferred for repairing knee or hip joints. Accordingly, just as an orthopedic supply company can make and sell an assortment of braided anchoring sutures with a range of traits, it also can make and sell an assortment of ratcheting suture anchors, wherein each particular type of ratcheting anchor has been tested and shown to perform optimally when matched up with a particular type of braided suture.

With regard to all candidate mechanisms disclosed herein, the hardness, rigidity, elastomeric, "gripping", and other physical traits of the devices that are included in the ratcheting mechanisms disclosed herein can be controlled, over the entire spectrum of interest. By way of illustration, most gears and other surfaces made of metal alloys that are known and approved as biocompatible would be classified as rigid and non-yielding, when the types of relatively low-level forces of interest herein are involved. Somewhat less hard and rigid materials (which may be able to provide a better "grip" on braided suture strands made out of at least some types of candidate materials) can be provided by moderately hard polymers, such as the type of molded nylon that is used to manufacture gears that are used in various types of toys, small appliances, and other "light duty" uses. Lower levels of hardness (which translate into increasing levels of deformation and elasticity, and in some cases, to potentially higher levels of "gripping ability" when interacting with braided sutures) can also be achieved by methods and recipes known to polymer chemists, as shown by the availability of hard, medium, and soft rubber and rubber-like polymers that cover a very wide range of mechanical and behavioral properties. Each of those candidate materials will establish its own gripping and performance traits, if incorporated into a ratcheting mechanism that has a ridged or other non-smooth surface for gripping and securing a strand of braided suture material. Accordingly, a routine testing program, which evaluates a range of such materials in the type of ratcheting designs disclosed herein, can quickly identify optimal combinations of ratcheting mechanisms and braided suture strands, for use as described herein.

Figure 5:
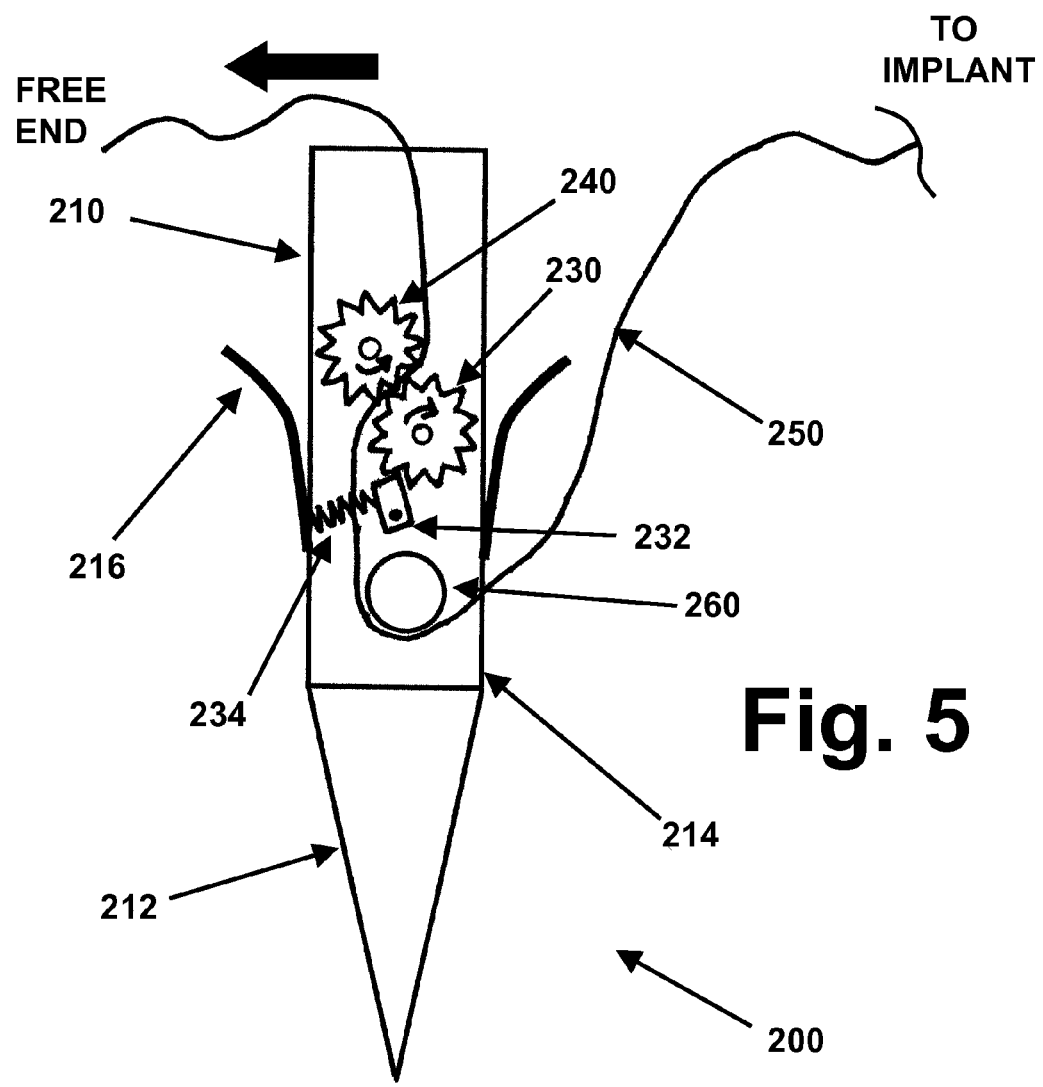
FIG. 5 depicts a miniaturized double-gear ratchet system within a suture anchor, which will allow a surgeon to adjust, in a stepwise manner, the tension on an anchoring and/or reinforcing suture strand.

Those comments involve certain principles that will apply to the design and selection of ratcheting mechanisms as disclosed herein. Turning to specific types of ratcheting mechanisms that will merit evaluation and testing for use with braided suture strands having a range of thicknesses and other traits, FIG. 5 depicts a ratcheting suture anchor 200, enclosed within a shell 210. In most embodiments, the shell component or subassembly 210 will contain a pointed insertion end 212, and an outer cylinder 214 (which can also be called a sleeve, barrel, hood, or similar terms).

Either or both of the pointed end 212 and the outer cylinder 214 can be provided with external threads, a ridged sawtooth-like surface, or other any other surface component, texture, or shape that will help ensure stable anchoring, either in hard bone, or in soft tissue if the suture anchor is intended for such use. One such anchoring means, which is shown in FIG. 5, comprises a set of barbs 216, which will be made of a spring-type material, which can be generally but not completely flattened against the outer cylinder 214 while the anchor is being inserted into a bone. Once the anchor 200 has reached its proper depth within bone tissue, the slightly curled or angled tips of the barbs 216 will tend to dig into the bone or other tissue and will generate resistance, if a retracting force (such as tensile force imposed on the suture strand) attempts to pull the anchor out of the bone. At least two and preferably three or four barbs 216 should be provided, in a symmetric and outwardly-pointing radial arrangement around the circumference of outer cylinder 214.

The ratchet mechanism 220 inside anchor 200 is a double-gear mechanism, with a first rotatable gear 230 which interacts with pawl component 232, and a second rotatable gear 240. A compressible spring 234 is shown, which presses pawl 232 against the teeth of gear 230; that type of spring is solely for illustration, and a simpler type of spring mechanism (such as a single-leaf spring, a rubberized elastomeric axle, etc.) normally will be used, to reduce any risk of obstruction by bone chips or other fragments. If desired, pawl components which will block rotation in a non-allowed direction can be provided for both gears.

The teeth of both of the two gears 230 and 240 will attempt to press against each other, due to either or both of two factors: (i) spacing of their axles; or, (ii) by using a spring-loaded mechanism to press gear 240 closer to gear 230. This will cause both sets of teeth to press against (and "bite" into) the surface of braided suture strand 250, which passes between the two gears 230 and 240. In a suitably-designed anchor which interacts with a strong but deformable braided cable (which presumably will be woven from strands of either a ductile alloy or a high-strength polymer such as a ultra-high-molecular-weight polyethylene or polyaramid fibers), this will ensure that the two gears will grip and hold the suture strand in a manner which will be strong and secure, but which will not cut into, cut through, or damage the suture strand.

An optional pivot or pulley component 260 is also shown in FIG. 5. If desired, it can be used to position and align the suture strand 250. However, that component is not essential, and suture strand 250 can simply be wrapped around gear 230.

This type of anchor 200 can be manufactured as a single unitary device, if it is designed to be driven (such as by gently tapping the anchor into a pre-drilled hole in a bone) into a bone or other tissue in a manner that does not require a rotational screwing motion.

Alternately, a ratcheting anchor can be designed and manufactured to include: (i) an outer component which will be emplaced first, and which can be called a receptacle or similar terms; and, (ii) an insert component, which will be inserted into and coupled to the receptacle. If desired, the receptacle component can be provided with external screw threads on a portion of its outer surface. Internally, it can contain a sawtooth surface, bayonet-type fitting, or other suitable component or means, to allow the insert component to be pushed into the receptacle or sleeve in a manner that will lock the insert in place.

Figure 6:
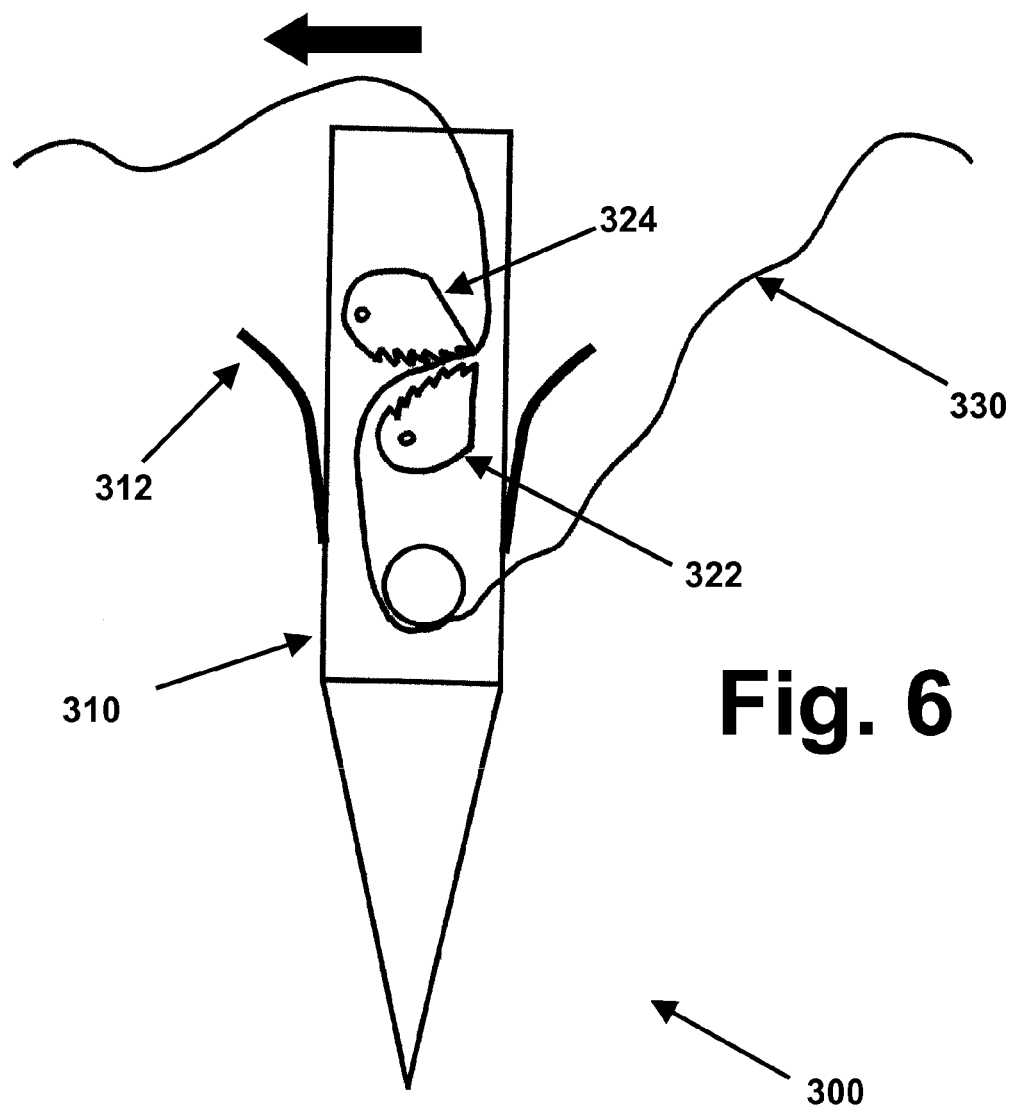
FIG. 6 depicts a knotless suture anchor with an internal ratcheting mechanism, containing two axle-mounted non-circular gripping components which will act in a manner comparable to the types of cam-cleat devices that are used to adjust and tension ropes on sailboats.

FIG. 6 depicts an alternate design for a ratcheting suture anchor 300. This design uses a similar outer shell 310 with anchoring barbs 312. Internally, it contains two axle-mounted non-circular (cam shaped) gripping gears 322 and 324, which will contact and press against suture strand 330, which passes between the two gears 322 and 324. Both of the gears will be mounted on their axles using a suitable spring-loading mechanism, such as a coiled spring or an elastomeric polymer component, to rotate at least one and preferably both of the two gears toward each other, so that their toothed or otherwise irregular surfaces will always be subjected to at least some level of force which pushes the two gears inwardly, toward each other. Accordingly, this mechanism will allow a braided suture strand to be pulled through the gears in one direction with little resistance; however, if the suture strand attempts to travel in the other direction, the teeth and gears will grip the surface of the suture strand, in a manner directly comparable to the "cam cleat" devices that are described in the Background section, which are used to adjust and tension ropes on sailboats.

Figure 7:
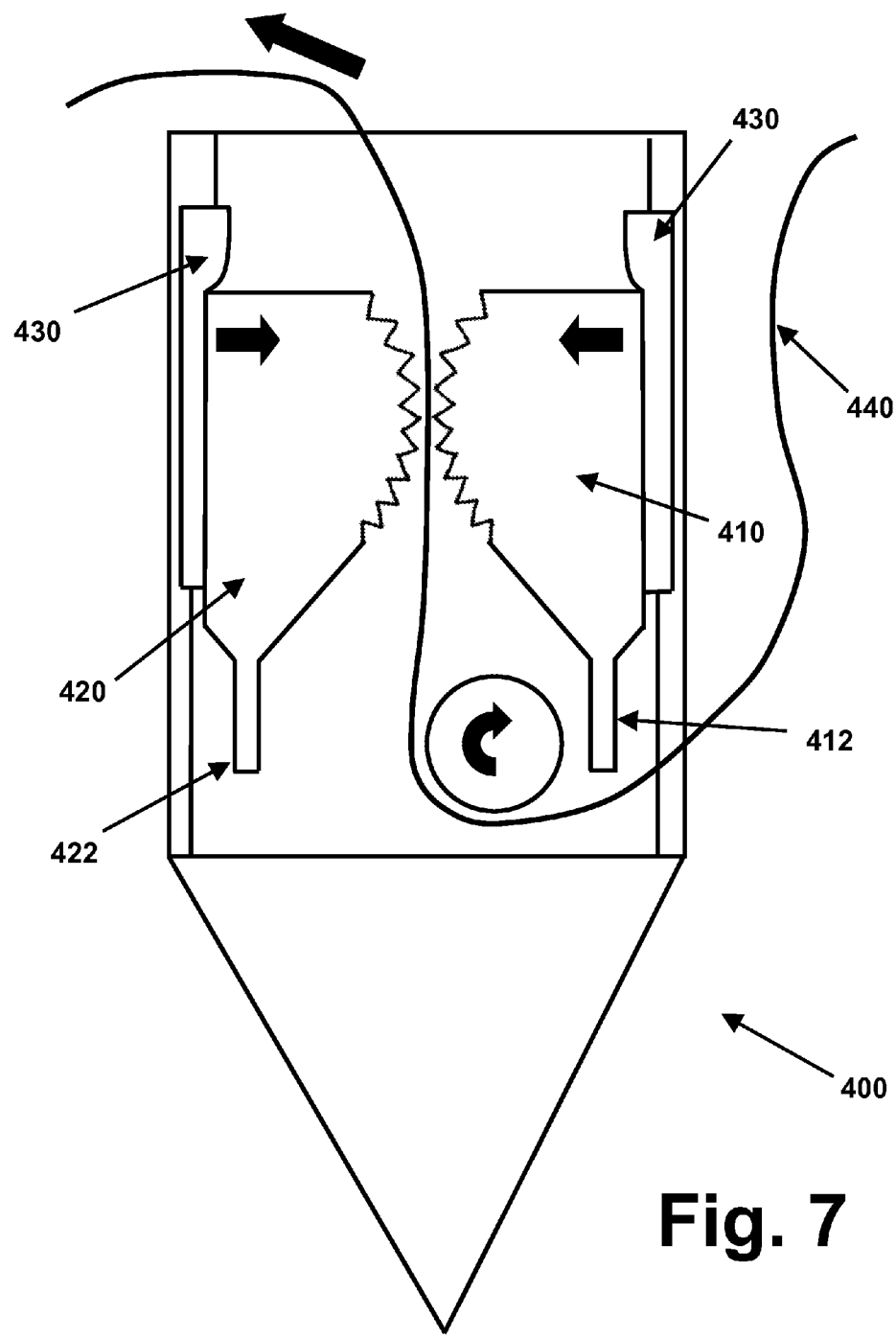
FIG. 7 depicts a cam-cleat mechanism in which the two cam-shaped gears are mounted on flaps or extensions, rather than axles, and are pressed inwardly by a surrounding sleeve made of an elastomeric polymer.

It should also be noted that either or both of the two gears can be mounted in different ways, in a miniaturized device such as a suture anchor. For example, rather than being mounted on spring-mounted axles, FIG. 7 depicts a cam cleat system 400 in which both of the two cam-shaped gears 410 and 420 are mounted at the ends of spring-type extensions 412 and 422, which are molded from a stiff but somewhat yielding polymeric material. In addition, the two gears 410 and 420 are positioned within a sleeve or collar device 430, which is made of an elastomeric polymer which has a substantial thickness. Because of the sizes and dimensions of the gears and the rubbery sleeve, the sleeve will constantly exert an inward-directed pressure which attempts to press the toothed faces of the two cammed gears toward each other, in a manner which will cause both of the toothed gear faces to press against, and bite into, the anchoring suture 440. The suture strand 440 can be pulled through the cammed gears 410 and 420, in the direction indicated, with minimal or moderate resistance. However, if and when a retracting force tries to pull the suture strand in the opposite direction, any movement of the suture strand will also pull the two cammed gears downward, and closer together. This will cause the toothed gear faces to press against each other even harder, in a manner which will effectively lock the suture strand in position, and prevent it from traveling in the non-allowed direction.

Figure 8:
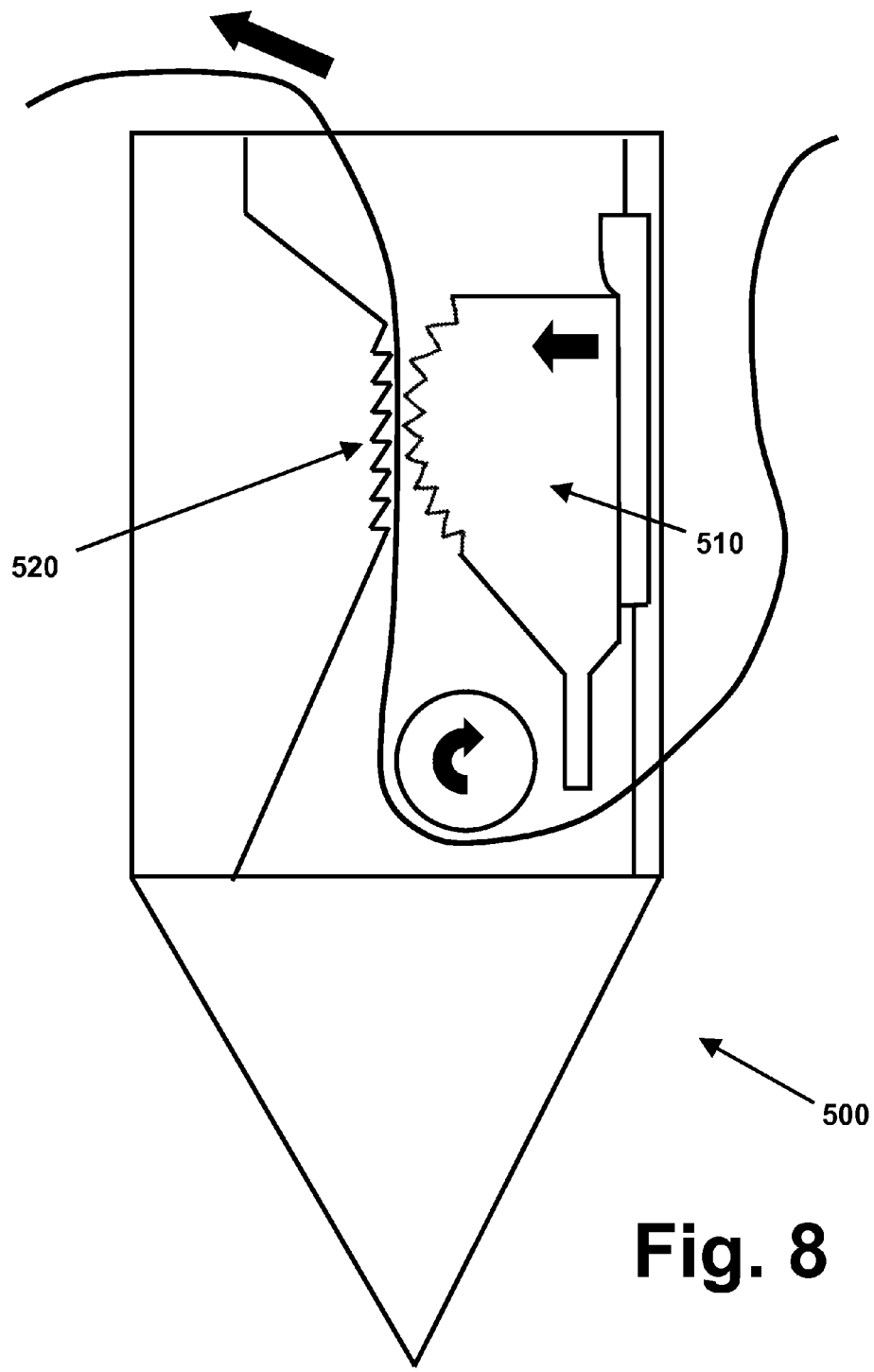
FIG. 8 depicts a knotless suture anchor containing a single axle-mounted ratcheting component, which will interact with a fixed sawtooth surface on an interior wall of the suture anchor to establish ratcheting control over a braided suture strand that passes through the suture anchor.

FIG. 8 depicts a ratcheting suture anchor 500 containing a single non-circular cam-shaped gear 510. Rather than interacting with a second gear, the toothed surface of gear 510 will interact with a sawtoothed or other non-smooth surface 520, which has been molded into an interior wall of the suture anchor shell. In this manner, a single gear 510 can establish the same type of ratcheting control, over a braided suture strand, that is provided by a two-gear system such as shown in FIG. 6 or 7.

Figure 9:
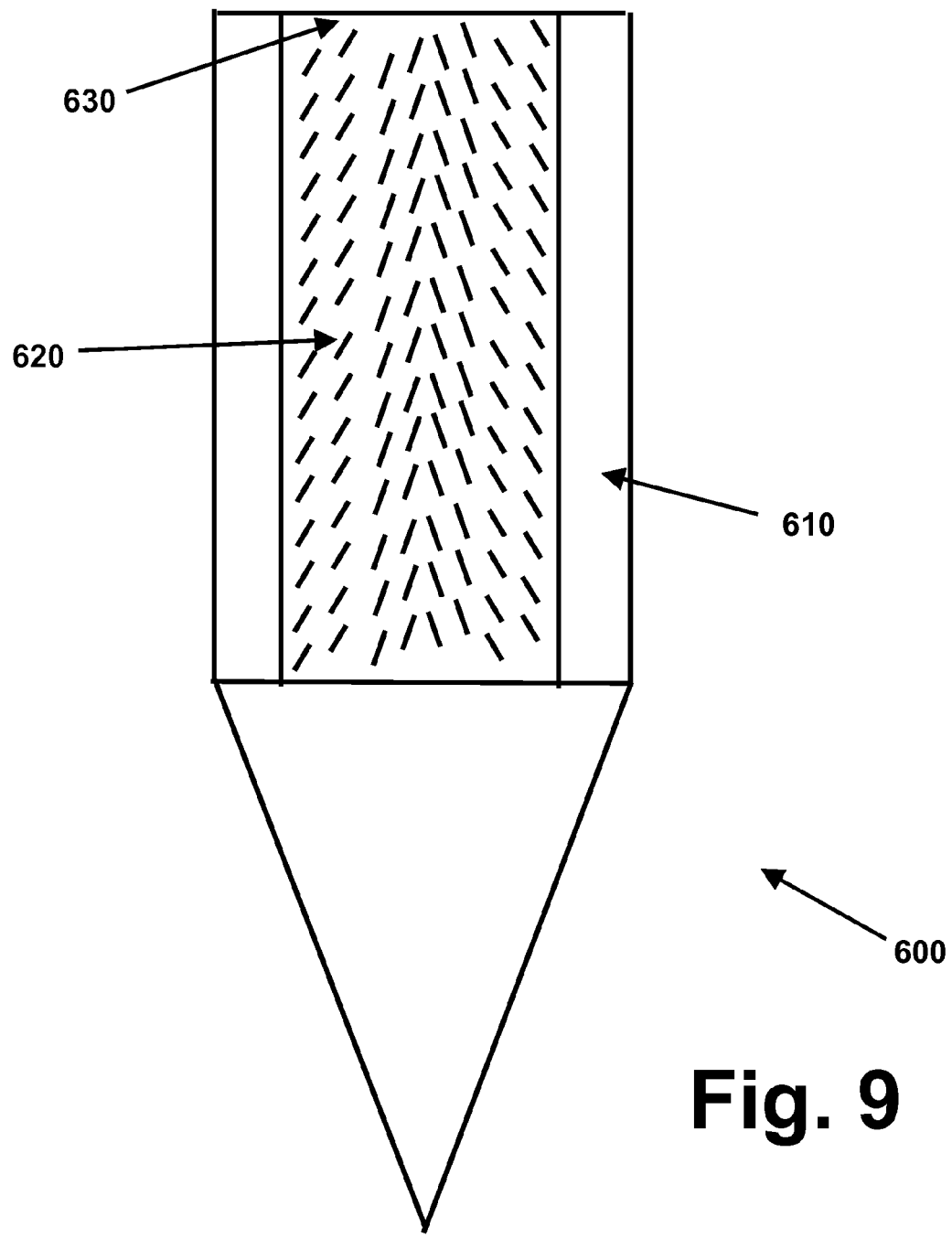
FIG. 9 depicts a cylindrical sleeve device with numerous stiff bristles lining the internal surface of the sleeve, angled toward the outlet end of the sleeve. A braided suture strand can be pulled through the sleeve toward the outlet end, with minimal resistance. However, if a tensile force attempts to pull the suture strand in the opposite direction, bristles will become lodged in the interwoven surface of the braided strand, and will prevent the strand from moving in the non-allowed direction.

FIG. 9 depicts a ratcheting suture anchor 600 which comprises a cylindrical sleeve 610 that contains numerous stiff bristles 620, lining the internal surface of the sleeve. All of the bristles 620 are angled toward the outlet end 630 of the sleeve 610. A braided suture strand (not shown in FIG. 9) can be pulled through sleeve 610, toward outlet end 630, with only minimal resistance. However, if a tensile force attempts to pull the braided suture strand in the opposite direction, at least some of the bristles will become lodged in the interwoven surface of the braided strand, and will prevent the strand from moving in the non-allowed direction.

Accordingly, when restated in terms suited for a patent claim, the types of anchoring devices disclosed herein, to be covered as part of this invention, must be designed, sized, and suited for permanent attachment to at least one type of internal tissue (which can be either hard bone, or soft tissues), wherein the anchoring device has a passageway and a ratcheting mechanism which will enable a suture strand to pass through the anchoring device in a manner which will: (a) enable a surgeon to gradually snug and then tighten a suture strand, by pulling the suture strand through the anchoring device in a first direction; and, (b) prevent the suture strand from traveling through the anchoring device in an opposing direction, which if not prevented would allow the suture strand to become looser; and wherein the anchoring device enables a suture strand to be initially pulled snug to a first level of positioning tension, and later tightened to a second level of final tension during a final tensioning procedure.

Crimping Anchors

An additional type of design for ratcheting suture anchors has been conceived by the Applicant herein, which merits attention in its own right. These types of anchors are referred to herein as "crimping" anchors, since they will be designed to be deformed, during an installation procedure, in a manner which will generate a ratcheting-type grip on a suture strand which will not exist during the initial steps of emplacement.

Figure 10:
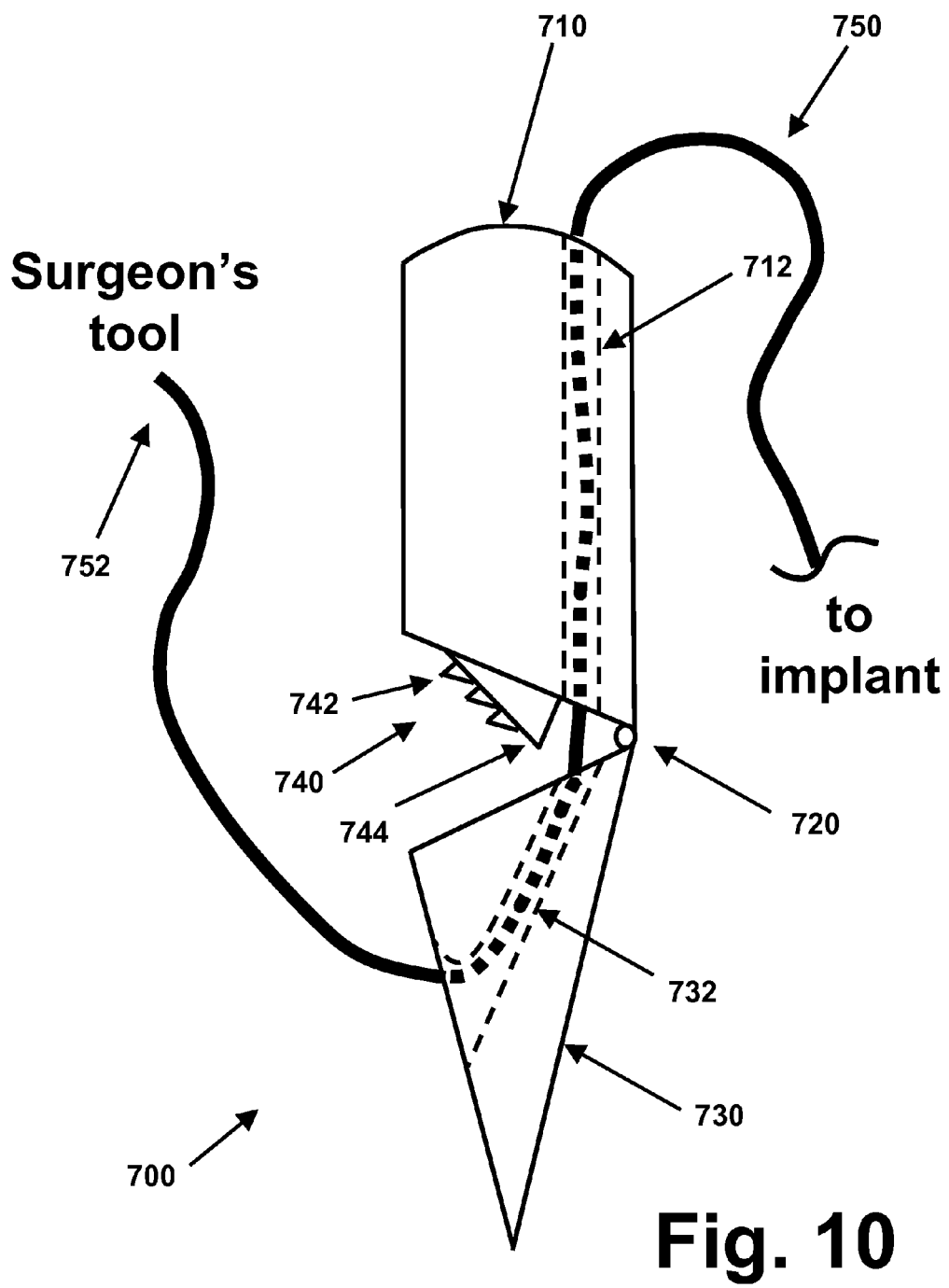
FIG. 10 depicts an anchoring suture which passes through a cylindrical anchoring component that is designed to flex in a manner which will effectively crimp the suture strand, in a manner which will secure it to the anchoring device.
Figure 11:
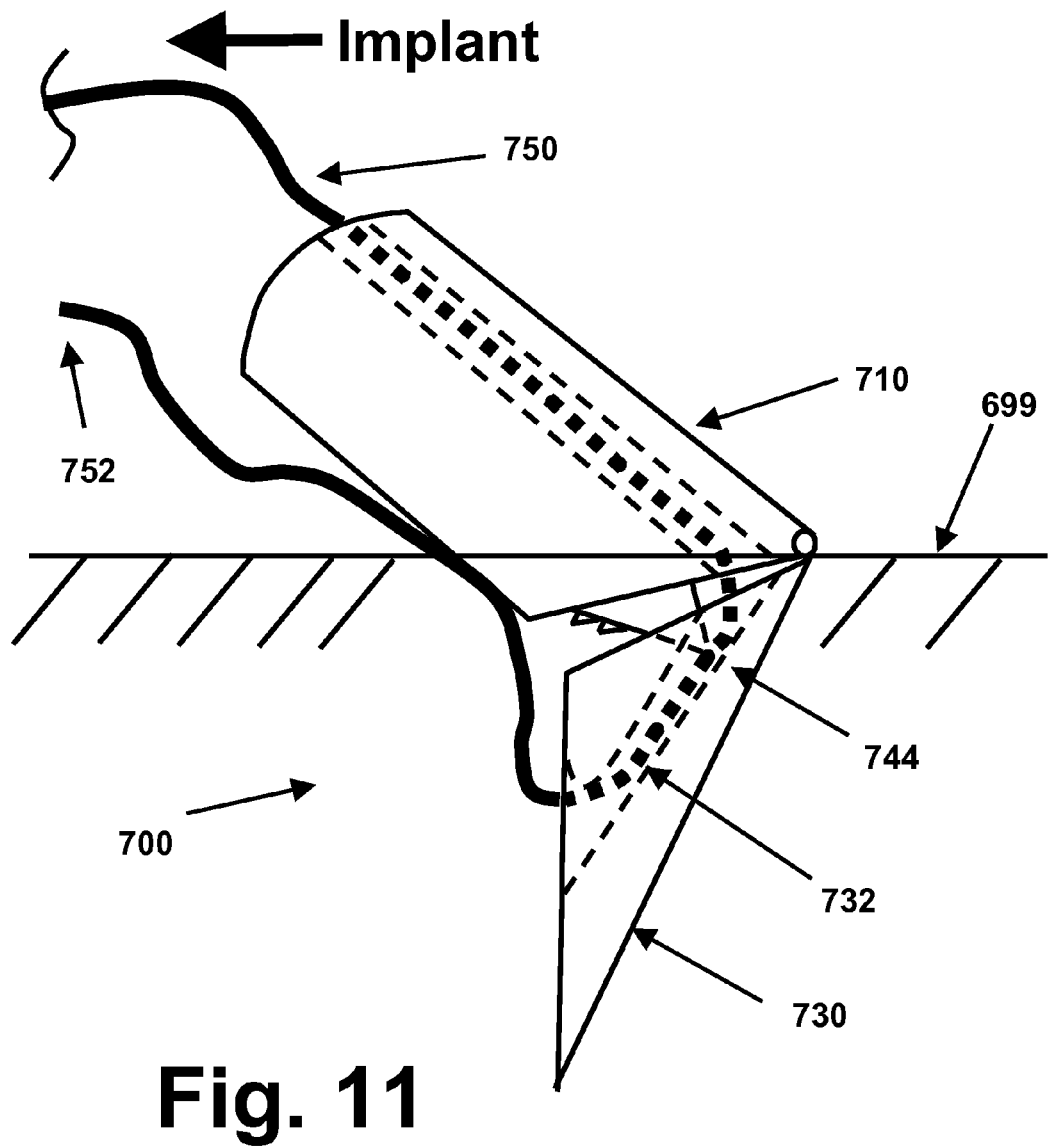
FIG. 11 depicts an anchoring suture passing through the same crimping anchor shown in FIG. 10, after the crimping anchor has been driven into a bone surface.

One such design is depicted in FIGS. 10 and 11, which depict the same anchoring device 700, prior to installation (FIG. 10), and after being driven into a bone surface 699 (FIG. 11).

In its uncrimped, undeformed shape, anchor 700 comprises a generally cylindrical barrel portion 710. It also contains a generally conical pointed segment 730, which also has a conduit 732 passing through it. The two main segments 710 and 730 are coupled to each other by a relatively thin segment of deformable material at juncture 720 (which is depicted as a circle in FIG. 10 for purposes of illustration, since it will provide a "pivot point" comparable to a hinge).

Barrel portion 710 has a conduit 712 (which can also be called a tunnel, orifice, passageway, or similar terms) passing through it longitudinally; pointed segment 730 has a similar conduit 732 passing through it. A single anchoring suture strand 750 will be laced through both of the conduit segments 712 and 732, which will have their adjacent openings aligned in both the uncrimped and crimped arrangements. One end of suture strand 750 will be securely affixed to a surgical implant device (such as implant device 110, as shown in FIGS. 3 and 4), while strand end 752 will be a "free end" which is accessible to a surgeon.

Anchoring device 700 also is provided with a "crimping ramp" 740, which has a notched, ridged, sawtooth, or other engaging surface 742, and a crimping corner or edge 744. As indicated in FIG. 11, when anchoring device 700 is bent and crimped, upon installation, the edge or corner 744 of crimping ramp 740 will press and pinch against one side of the suture strand 750; if desired, an accommodating slot can be provided as part of the "mouth" end of conduit 732 which passes through pointed segment 730.

Accordingly, when anchoring device 700 is first emplaced into bone surface 699 (this can be done with the aid of a pre-drilled pilot hole when appropriate, or the anchor can be driven into a bone surface with no pilot hole, by using a device comparable to a stapler or nail gun) there will be relatively little or no crimping together of the two segments 710 and 730, and the surgeon will be able to pull on the free end 752 of anchoring suture 750, with relatively little resistance.

As the surgeon begins to initially tighten suture strand 750 into a gentle and non-final "snugged" level of tension and tightness, the tension exerted on the strand 750 (leading to the immobilized implant device, in a nearby location on the surface of the bone) will begin to initiate a bending and crimping process, which will cause the barrel component 710 to bend or fold over, moving it closer to pointed segment 730. As the extent of bending and crimping between the anchor segments 710 and 730 increases, the edge or corner 744 of crimping ramp 740 will begin to press against and pinch the suture strand 750, in a progressively tighter manner. When the surgeon has completed the final tightening adjustments for that anchoring suture strand, he or she can press or tap down the exposed upper corner of the anchor 700, in a way which will increase the pressure imposed by the edge or corner 744 of crimping ramp 740, against suture strand 750, thereby effectively locking suture strand 750, inside the conduit passing through anchoring device 700, with a desired level of final tensioning.

Various other modifications can be made to this type of crimping anchor device, if desired. For example, a second suture conduit can be provided, either within pointed component 730, or as a groove which travels along an external surface, to enable easier pulling and travel of the free end 752 of suture strand 750. However, at the current time, prior to actual fabrication and testing of such devices, the Applicant herein anticipates that: (i) such a conduit will not be necessary; (ii) an experienced orthopedic surgeon will not have serious difficulty in pulling a suture strand through a relatively tight gap between a bone surface, and an anchoring device; and, (iii) the absence of any such additional conduit can help ensure that the tension in the suture strand, created by the surgeon during installation of the implant, will last until tissue ingrowth into the anchoring surface of the implant has reached a mature and stable level.

Handling Long Threads, and Preserving a Natural "Feel"

All of the ratchet mechanisms disclosed herein will allow a suture strand to pass entirely through an anchor device, in a manner which will provide a "free end" of the suture strand. This can provide two potentially important benefits, compared to the type of rotating ratchet mechanism disclosed in the published applications by Van der Burg et al.

First, the "direct pass-through" nature of the ratchet mechanisms disclosed herein will allow substantially longer suture strands to be used, for initial anchoring and preliminary reinforcing of a cartilage-replacing implant device, compared to a rotating ratchet system which would need to stuff long suture strands inside miniaturized cylinders that are kept as small as possible. The types of flexible cartilage-replacing implant devices being developed by the Applicant herein will pose substantial challenges, especially to surgeons must learn how to use them effectively. A set of relatively long and easily-reachable suture strands, positioned at key locations around the periphery of an implant, will effectively provide a set of "handles" that can be used by a surgeon to help the surgeon manipulate and position an implant, inside a joint which is being manipulated with only limited arthroscopic access.

It should also be noted that the suture strands which are coupled to an implant can be color-coded, to provide a surgeon with an additional set of visual cues, to help the surgeon complete the surgical procedure quickly and effectively.

Secondly, since all of the ratchet mechanisms disclosed herein will allow the "free end" of a suture strand to be grasped and pulled by the surgeon, these designs can preserve a normal and natural "feel", which most arthroscopic surgeons would prefer to have, during a tightening procedure. By contrast, a rotating ratchet mechanism, as disclosed in published application 2010/0063542 (Van der Burg et al) will need to be driven by some type of wrench or similar powered tool. Furthermore, in a rotating ratchet system which must be driven by a powered wrench, there is some level of risk that the accumulation of a significant length of suture strand, in a narrow and tightly constrained gap between an internal rotating device and a surrounding sleeve, might cause the rotation and responsiveness of the mechanism to be altered, and distorted, in ways that cannot be fully predicted or controlled if a substantial length of suture strand is involved.

Finally, it should be noted that the relatively simple "direct pass-through" nature of the ratchet mechanisms disclosed herein can enable various designs and methods for momentarily releasing the grip of a ratchet mechanism on a suture strand, in a way that will allow the tension in the strand to be reduced, if necessary. As just one example, a small sleeve made of smooth-surfaced plastic, with a slit passing through it lengthwise, can be fitted onto the surface of a suture strand, immediately "above" a ratchet mechanism. If the smooth sleeve is pushed into the ratchet mechanism, it can create enough separation, between two gears or similar devices, to enable a suture strand to be pulled backward through the ratchet mechanism.

Use for Other Types of Surgical Repairs

It is believed by the Applicant that the types of ratcheting suture anchors which are disclosed herein will likely create and enable a variety of surgical uses, in addition to anchoring implants which are designed to replace cartilage in articulating joints.

As just one example, it is believed that these types of ratcheting suture anchors will enable improved approaches to repairing torn or otherwise damaged rotator cuffs, in human shoulder joints. As is well-known to orthopedic surgeons, a typical rotator cuff tear involves the detachment of certain tendon and ligament structures from the humerus (i.e., the long bone in the upper arm). When that type of tear occurs, the torn tendons and ligaments will tend to retract deeper into the shoulder joint, generally toward a patient's shoulder blade. Accordingly, a typical rotator cuff repair requires a surgeon to gently but firmly pull the torn tendon and ligament segments back in an "outward" direction, so that they can be reattached to the enlarged and rounded bone structure at the upper end of the humerus (which is called the "greater tuberosity of the humerus" by orthopedic surgeons). Once those damaged tendon and ligament segments have been pulled in an outward direction, back into their proper position, the surgeon does his best to reattach them to the end of the humerus.

Accordingly, if an orthopedic supply company can provide ratcheting suture anchors, as disclosed herein, to surgeons who perform rotator cuff repairs, the surgeons likely would find those new types of ratcheting anchor devices very useful during rotator cuff repairs.

Rotator cuff repairs offer just one example of how knotless suture anchors that have ratcheting capability, which can be exerted by simply pulling the free end of a suture strand through the anchor, would be very useful in various types of surgical and "sports medicine" repair of various types of connective tissues. If these types of suture anchors were readily available to surgeons and other physicians, other additional uses, at other locations in various limbs, joints, and body parts, would indeed be identified and developed.

Thus, there has been shown and described (i) a new and useful class of knotless suture anchors with ratcheting capability, and (ii) a new and useful class of surgical implant devices which incorporate such ratcheting suture anchors. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

What is claimed is:

1. An anchoring device for use in surgical installation of an implant, wherein the implant is to be connected to the anchoring device by a suture, comprising:
    an anchoring component having a barrel portion and a pointed segment coupled to the barrel portion, wherein the pointed segment is configured to be embedded in tissue,
    wherein the barrel portion and the pointed segment are aligned in an uncrimped state of the anchoring device and have suture passages therethrough, and wherein the barrel portion and the pointed segment are coupled to one another at a juncture at which the barrel portion is bendable laterally out of alignment with the pointed segment;
    a crimping structure on one of the barrel portion and the pointed segment, configured to bear against the other of the barrel portion and the pointed segment when the barrel portion is bent over laterally out of alignment with the pointed segment, thereby crimping a suture strand passing through the suture passages and between the barrel portion and the pointed segment;
    wherein tightening the suture strand by pulling the suture strand through the anchoring device in a first direction to a tension sufficient to bend over the barrel portion, causes the crimping structure to fix the suture strand to the anchoring device.

2. The anchoring device of claim 1, wherein the crimpinq structure comprises at least one surface configured to engage a surface of a braided suture strand in a gripping manner.

3. The anchoring device of claim 1, wherein the crimpinq structure comprises at least one of a ramp, notch, ridge and saw tooth bearing against the suture strand when the barrel is bent over laterally.

4. A surgical implant device, comprising:
    a surgical implant with an anchoring structure including at least one anchoring suture emerging from said implant device, and an anchoring component having a barrel portion and a pointed segment coupled to the barrel portion, wherein the pointed segment is configured to be embedded in tissue,
    wherein the barrel portion and the pointed segment are aligned in an uncrimped state of the anchoring device and have suture passages therethrough, and wherein the barrel portion and the pointed segment are coupled to one another at a juncture at which the barrel portion is bendable laterally out of alignment with the pointed segment;
    a crimping structure on one of the barrel portion and the pointed segment, configured to bear against the other of the barrel portion and the pointed segment when the barrel portion is bent over laterally out of alignment with the pointed segment, thereby crimping a suture strand passing through the suture passages and between the barrel portion and the pointed segment;
    wherein tightening the suture strand by pulling the suture strand through the anchoring device in a first direction to a tension sufficient to bend over the barrel portion, causes the crimping structure to fix the suture strand to the anchoring device.

5. The surgical implant device of claim 4, wherein the crimping structure comprises at least one surface configured to engage a surface of a braided suture strand in a gripping manner.

6. The surgical implant device of claim 4, wherein the crimping structure comprises at least one of a ramp, notch, ridge and saw tooth bearing against the suture strand when the barrel is bent over laterally.

* * * * *